United States Patent
Nikrad et al.

(10) Patent No.: US 9,316,647 B2
(45) Date of Patent: Apr. 19, 2016

(54) APTAMERS AND DIAGNOSTIC METHODS FOR DETECTING THE EGF RECEPTOR

(71) Applicant: SomaLogic, Inc., Boulder, CO (US)

(72) Inventors: Malti P. Nikrad, Boulder, CO (US); Bharat Nathu Gawande, Lafayette, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 14/365,332

(22) PCT Filed: Dec. 28, 2012

(86) PCT No.: PCT/US2012/072101
§ 371 (c)(1),
(2) Date: Jun. 13, 2014

(87) PCT Pub. No.: WO2013/102101
PCT Pub. Date: Jul. 4, 2013

(65) Prior Publication Data
US 2014/0296501 A1    Oct. 2, 2014

Related U.S. Application Data

(60) Provisional application No. 61/582,111, filed on Dec. 30, 2011, provisional application No. 61/649,168, filed on May 18, 2012, provisional application No. 61/655,404, filed on Jun. 4, 2012.

(51) Int. Cl.
*C07H 21/04* (2006.01)
*G01N 33/574* (2006.01)
*C12N 15/115* (2010.01)

(52) U.S. Cl.
CPC .......... *G01N 33/57492* (2013.01); *C07H 21/04* (2013.01); *C12N 15/115* (2013.01); *C12N 2310/16* (2013.01); *C12N 2310/317* (2013.01); *C12N 2310/3513* (2013.01); *C12N 2310/3517* (2013.01); *C12N 2320/10* (2013.01); *G01N 2333/71* (2013.01); *G01N 2800/52* (2013.01)

(58) Field of Classification Search
CPC .............................. C07H 21/04; C12N 15/115
See application file for complete search history.

(56) References Cited

U.S. PATENT DOCUMENTS

| | | | |
|---|---|---|---|
| 5,428,149 A | 6/1995 | Eaton | |
| 5,582,981 A | 12/1996 | Toole et al. | |
| 5,719,273 A | 2/1998 | Tu et al. | |
| 5,756,291 A | 5/1998 | Griffin et al. | |
| 5,945,527 A | 8/1999 | Tu et al. | |
| 7,855,054 B2 | 12/2010 | Schneider et al. | |
| 7,947,447 B2 | 5/2011 | Zichi et al. | |
| 7,964,356 B2 | 6/2011 | Zichi et al. | |
| 8,404,830 B2 * | 3/2013 | Zichi | C12Q 1/6811 536/24.5 |
| 8,975,026 B2 * | 3/2015 | Zichi | C12N 15/1048 424/9.1 |
| 8,975,388 B2 * | 3/2015 | Zichi | C12Q 1/6811 536/23.1 |
| 9,125,930 B2 * | 9/2015 | De Franciscis | A61K 31/7088 |
| 2004/0142384 A1 | 7/2004 | Cohen et al. | |
| 2007/0105142 A1 | 5/2007 | Wilhelm et al. | |
| 2007/0166741 A1 | 7/2007 | Heil et al. | |
| 2008/0261829 A1 | 10/2008 | Harvey et al. | |
| 2009/0042206 A1 * | 2/2009 | Schneider | C12Q 1/6832 435/6.12 |
| 2010/0021899 A1 | 1/2010 | Ikebukuro et al. | |
| 2010/0166776 A1 * | 7/2010 | Buck | A61K 31/436 424/172.1 |
| 2010/0203043 A1 | 8/2010 | Ree et al. | |
| 2010/0285479 A1 | 11/2010 | Jenison | |
| 2011/0082286 A1 * | 4/2011 | Zichi | C12Q 1/6811 536/23.1 |
| 2012/0207744 A1 * | 8/2012 | Mendlein et al. | 424/130.1 |

FOREIGN PATENT DOCUMENTS

WO    WO 2012/049112    4/2012
WO    WO 2013/012096    7/2013

OTHER PUBLICATIONS

Gold et al. PLoS 2010 5: pp. 1-17.*
Gold et al. (Jan. 1, 1995) Harvey Lectures 91:47-57, "The SELEX Process: A Surprising Source of Therapeutic and Diagnostic Compounds".
IPRP issued Jul. 10, 2014 in PCT/US2012/072101.
ISR and Written Opinion mailed Apr. 23, 2013 in PCT/US2012/0072101.
Li et al. (Jun. 2011) PLoS ONE. 1-4 6(6);e20299, pp. 1-10. doi:10.1371/journal.pone.0020299; "Inhibition of Cell Proliferation by an Anti-EGFR Aptamer".
Vaught et al. (Mar. 2010) J.Am. Chem. Soc. ePub, 132(12):4141-4151:4142, "Expanding the Chemistry of DNA for In Vitro Selection".
Vaught, Jonathan David, Thesis Oct. 2008, "Enhancing the Functionality of Nucleic Acids", pp. 1-135.
Wan et al. (Nov. 2010) Cancer Res. 70(22):9371-9380, "Surface-Immobilized Aptamers for Cancer Cell Isolation and Microscopic Cytology".
Zichi et al. (Mar. 7, 2008) Current Opinion in Chemical Biology 12(1):78-85, "Proteomics and diagnostics: Let's Get Specific, again".
Davies et al., "Unique motifs and hydrophobic interactions shape the binding of modified DNA ligands to protein targets", PNAS, vol. 109, No. 49, pp. 19971-19976, published on Dec. 4, 2012.
Espositio et al. (Sep. 2011) PloS One, 6(9):1-12 E2407 1, "A neutralizing RNA aptamer against EGFR causes selective apoptotic cell death".
European Search Report mailed Jun. 8, 2015 in EP 12863462.3.
Ohuchi et al. (2006) Biochimie 88:897-904, "Selection of RNA aptamers against recombinant transforming growth factor-β type III receptor displayed in cell surface".
Wan et al. (Dec. 2011) The Journal of Physical Chemistry 115(47):13891-13896, "Velocity effect on aptamer-based circulating tumor cell isolation in microfluidic devices".

\* cited by examiner

*Primary Examiner* — Brian Whiteman
(74) *Attorney, Agent, or Firm* — Swanson & Bratschun, L.L.C.

(57) ABSTRACT

The present invention provides aptamers that specifically bind to the EGF receptor in a sample, and diagnostic and analytical methods using those aptamers.

10 Claims, 18 Drawing Sheets

| Aptamer No. | Target | SELEX | Base Comp | Kd (M) | SynReqDate |
|---|---|---|---|---|---|
| 2677-1_0 | ERBB1 | S180 R9 S26 | ACGT | - | 11/3/2009 |
| 2677-1_1 | ERBB1 | S180 R9 S26 | ZACGT | 1.23E-10 | 6/1/2009 |
| 2677-1_2 | ERBB1 | S180 R9 S26 | ZACGT | - | 6/29/2010 |
| 2677-1_3 | ERBB1 | S180 R9 S26 | ZACGT | 2.83E-09 | 6/29/2010 |
| 2677-1_4 | ERBB1 | S180 R9 S26 | ZACG | 5.26E-10 | 6/29/2010 |
| 2677-1_5 | ERBB1 | S180 R9 S26 | ZACGT | flat | 6/29/2010 |
| 2677-1_6 | ERBB1 | S180 R9 S26 | ZACGT | 3.11E-09 | 6/29/2010 |
| 2677-1_7 | ERBB1 | S180 R9 S26 | ZACGT | - | 8/10/2010 |
| 2677-1_8 | ERBB1 | S180 R9 S26 | ZACGT | - | 8/10/2010 |
| 2677-1_9 | ERBB1 | S180 R9 S26 | ZACGT | - | 8/10/2010 |
| 2677-1_10 | ERBB1 | S180 R9 S26 | ZACGT | - | 8/10/2010 |
| 2677-1_11 | ERBB1 | S180 R9 S26 | ZACGT | - | 8/10/2010 |
| 2677-1_12 | ERBB1 | S180 R9 S26 | ZACGT | - | 8/10/2010 |
| 2677-1_13 | ERBB1 | S180 R9 S26 | ZACGT | - | 8/10/2010 |
| 2677-1_14 | ERBB1 | S180 R9 S26 | ZACGT | - | 8/10/2010 |
| 2677-1_15 | ERBB1 | S180 R9 S26 | ZACGT | - | 8/10/2010 |
| 2677-1_16 | ERBB1 | S180 R9 S26 | ZACGT | - | 8/10/2010 |
| 2677-1_17 | ERBB1 | S180 R9 S26 | ZACGT | - | 8/10/2010 |
| 2677-1_18 | ERBB1 | S180 R9 S26 | ZACGT | - | 8/10/2010 |
| 2677-1_19 | ERBB1 | S180 R9 S26 | ZACGT | - | 8/10/2010 |
| 2677-1_20 | ERBB1 | S180 R9 S26 | ZACGT | - | 8/10/2010 |
| 2677-1_21 | ERBB1 | S180 R9 S26 | ZACGT | - | 8/10/2010 |
| 2677-1_22 | ERBB1 | S180 R9 S26 | ZACG | - | 8/10/2010 |
| 2677-1_23 | ERBB1 | S180 R9 S26 | ZACG | - | 8/10/2010 |
| 2677-1_24 | ERBB1 | S180 R9 S26 | ZACG | - | 8/10/2010 |

FIG. 4A

| Aptamer No.: | SeqID No.: | 5' Fixed | | | | | | | | | | | | | | | | 3' Fixed | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 1 | 2 | 3 | 4 | 5 | 6 | 7 | 8 | 9 | 10 | 11 | 12 | 13 | 14 | 15 | 16 | 17 | 18 |
| 2677-1_0 | 9 | C | C | A | C | G | C | T | G | G | G | T | G | G | G | T | C | G | A | A | C | A | C | C | A | A | C | C | G | A | G | A | A | C | G |
| 2677-1_1 | 10 | C | C | A | C | G | C | T | G | G | G | T | G | G | G | T | C | G | A | A | C | A | C | C | A | A | C | C | G | A | G | A | A | C | G |
| 2677-1_2 | 11 | | | | | | | T | G | | G | | G | G | G | T | C | G | A | A | C | A | | | | | | | | | | | | | |
| 2677-1_3 | 12 | | | | | | | | | | | | | | | | | G | A | A | C | A | C | C | A | A | C | | | | | | | | |
| 2677-1_4 | 13 | | | | | | | T | G | | G | T | G | G | G | T | C | G | A | A | C | A | C | C | A | A | | | | | | | | | |
| 2677-1_5 | 14 | | | | | | | | | | | | | | | | | G | A | A | C | A | C | C | A | A | C | | | | | | | | |
| 2677-1_6 | 15 | | | | | | | | | | | | | | | | | G | A | A | C | A | C | C | | A | | | | | | | | | |
| 2677-1_7 | 16 | | | | | G | C | T | G | G | G | T | G | G | G | T | C | G | A | A | C | A | C | C | A | A | C | C | G | A | G | A | A | | |
| 2677-1_8 | 17 | | | | | G | C | T | G | G | G | T | G | G | G | T | C | G | A | A | C | A | C | C | A | A | C | C | G | A | G | | | | |
| 2677-1_9 | 18 | | | | | G | C | T | G | G | G | T | G | G | G | T | C | G | A | A | C | A | C | C | A | A | C | C | G | | | | | | |
| 2677-1_10 | 19 | | | | | G | C | T | G | G | G | T | G | G | G | T | C | G | A | A | C | A | C | C | A | A | C | | | | | | | | |
| 2677-1_11 | 20 | | | | | G | C | T | G | G | G | T | G | G | G | T | C | G | A | A | C | A | C | C | A | | | | | | | | | | |
| 2677-1_12 | 21 | | | | | G | C | T | G | G | G | T | G | G | G | T | C | G | A | A | C | A | C | C | | | | | | | | | | | |
| 2677-1_13 | 22 | | | | | G | C | T | G | G | G | T | G | G | G | T | C | G | A | A | C | A | C | | | | | | | | | | | | |
| 2677-1_14 | 23 | | | | | G | C | T | G | G | G | T | G | G | G | T | C | G | A | A | C | A | | | | | | | | | | | | | |
| 2677-1_15 | 24 | | | | | G | C | T | G | G | G | T | G | G | G | T | C | G | A | A | C | | | | | | | | | | | | | | |
| 2677-1_16 | 25 | | | | | G | C | T | G | G | | | | G | | | | G | A | | | | | | | | | | | | | | | | |
| 2677-1_17 | 26 | | | | | | | | | | | | | | | | | G | A | A | C | A | C | C | A | A | C | C | G | A | G | A | A | | |
| 2677-1_18 | 27 | | | | | | | | | | | | | | | | | G | A | A | C | A | C | C | A | A | C | C | G | A | G | A | A | | |
| 2677-1_19 | 28 | | | | | | | | | | | | | | | | | G | A | A | C | A | C | C | A | A | C | C | G | A | G | A | A | | |
| 2677-1_20 | 29 | | | | | | | | | | | | | | | | | G | A | A | C | A | C | C | A | A | C | C | G | A | G | A | A | | |
| 2677-1_21 | 30 | | | | | | | | | | | | | | | | | G | A | A | C | A | C | C | A | A | C | C | G | A | G | A | A | | |
| 2677-1_22 | 31 | | | | | | | | | | | | | | | | | G | A | A | C | A | C | C | A | A | C | C | G | A | G | A | A | | |
| 2677-1_23 | 32 | | | | | | | | | | | | | | | | | G | A | A | C | A | C | C | A | A | C | C | G | A | G | A | A | | |
| 2677-1_24 | 33 | | | | | | | | | | | | | | | | | G | A | A | C | A | C | C | A | A | C | C | G | A | G | A | A | | |

▓ Selected Region on Following Pages

Selected Region

| Aptamer No.: | Seq ID No: | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| 2677-1_0 | 9  | A | T | C | G | A | G | G | T | T | G | T | G | G | G | T | C | G | G | A | T | T | G | T | T | G | G | A | T | T | C | T | T | T | A | A | G | T | T | G | G |
| 2677-1_1 | 10 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_2 | 11 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_3 | 12 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_4 | 13 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_5 | 14 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_6 | 15 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_7 | 16 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_8 | 17 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_9 | 18 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_10 | 19 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_11 | 20 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_12 | 21 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_13 | 22 | A | N | C | G | A | G | G | N | N | G | N | G | G | G | N | C | G | G | A | N | N | G | N | N | G | G | A | N | N | C | N | N | N | A | A | G | N | N | G | G |
| 2677-1_14 | 23 | A | N | C | G | A | G | G | N | N | G | N | G | G | G | N | C | G | G | A | N | N | G | N | N | G | G | A | N | N | C | N | N | N | A | A | G | N | N | G | G |

| 24 | 25 | 26 | 27 | 28 | 29 | 30 | 31 | 32 | 33 |
|---|---|---|---|---|---|---|---|---|---|
| G |   | G | G | G | G | G | G |   |   |
| G |   | G | G | G | G | G | G |   |   |
| N | N | N | N | N | N | N | N | G |   |
| N | N | N | N | N | N | N | N | G |   |
| G | G | G | G | G | G | G | G | N | G |
| A | A | A | A | A | A | A | A | N | G |
| A | A | A | A | A | A | A | A | G | N |
| N | N | N | N | N | N | N | N | A | N |
| N | N | N | N | N | N | N | N | A | G |
| N | N | N | N | N | N | N | N | N | A |
| C | C | C | C | C | C | C | C | N | A |
| N | N | N | N | N | N | N | N | N | N |
| N | N | N | N | N | N | N | N | C | N |
| A | A | A | A | A | A | A | A | N | N |
| G | G | G | G | G | G | G | G | N | C |
| G | G | G | G | G | G | G | G | A | N |
| N | N | N | N | N | N | N | N | G | N |
| N | N | N | N | N | N | N | N | G | A |
| G | G | G | G | G | G | G | G | N | G |
| N | N | N | N | N | N | N | N | N | G |
| N | N | N | N | N | N | N | N | G | N |
| A | A | A | A | A | A | A | A | N | N |
| G | G | G | G | G | G | G | G | N | G |
| G | G | G | G | G | G | G | G | A | N |
| C | C | C | C | C | C | C | C | G | N |
| N | N | N | N | N | N | N | N | G | A |
| G | G | G | G | G | G | G | G | C | G |
| G | G | G | G | G | G | G | G | N | G |
| G | G | G | G | G | G | G | G | G | C |
| N | N | N | N | N | N | N | N | G | N |
| G | G | G | G | G | G | G | G | G | G |
| N | N | N | N | N | N | N | N | N | N |
| N | N | N | N | N | N | N | N | G | G |
| G | G | G | G | G | G | G | G | N | N |
| G | G | G | G | G | G | G | G | N | G |
| A | A | A | A | A | A | A | A | G | N |
| G | G | G | G | G | G | G | G | G | N |
| C | C | C | C | C | C | C | C | A | G |
| N | N | N | N | N | N | N | N | G | A |
| 2677-1_15 | 2677-1_16 | 2677-1_17 | 2677-1_18 | 2677-1_19 | 2677-1_20 | 2677-1_21 | 2677-1_22 | 2677-1_23 | 2677-1_24 |

Z = 5-(N-benzylcarboxyamido)-2'-deoxyuridine (BndU)

FIG. 4B continued

Base = Uridine (U) or Cytidine(C) (attachment is to the 5-position)
K = R' group plus $(CH_2)_n$ connecting group, where n = 0-3 wherein

R'''' is selected from the group consisting of a branched or linear lower alkyl (C1-C20); hydroxyl (OH), halogen (F, Cl, Br, I); nitrile (CN); boronic acid (BO$_2$H$_2$); carboxylic acid (COOH); carboxylic acid ester (COOR''); primary amide (CONH$_2$); secondary amide (CONHR''); tertiary amide (CONR''R'''); sulfonamide (SO$_2$NH$_2$); N-alkylsulfonamide (SONHR'');

wherein

R'', R''' are independently selected from a group consisting of a branched or linear lower alkyl (C1-C2); phenyl (C6H5); an R'''' substituted phenyl ring (R''''C6H4); wherein R'''' is defined above; a carboxylic acid (COOH); a carboxylic acid ester (COOR''''); wherein R'''' is a branched or linear lower alkyl (C1-C20); and cycloalkyl; wherein R'' = R''' = (CH2)n; wherein n =2-10.

FIG. 5 continued

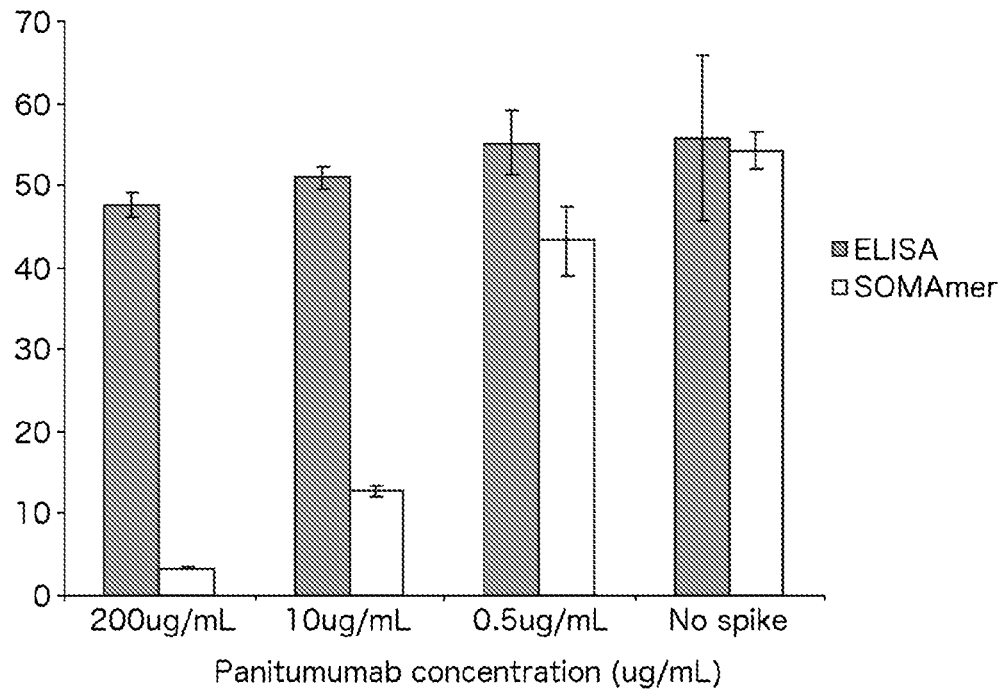
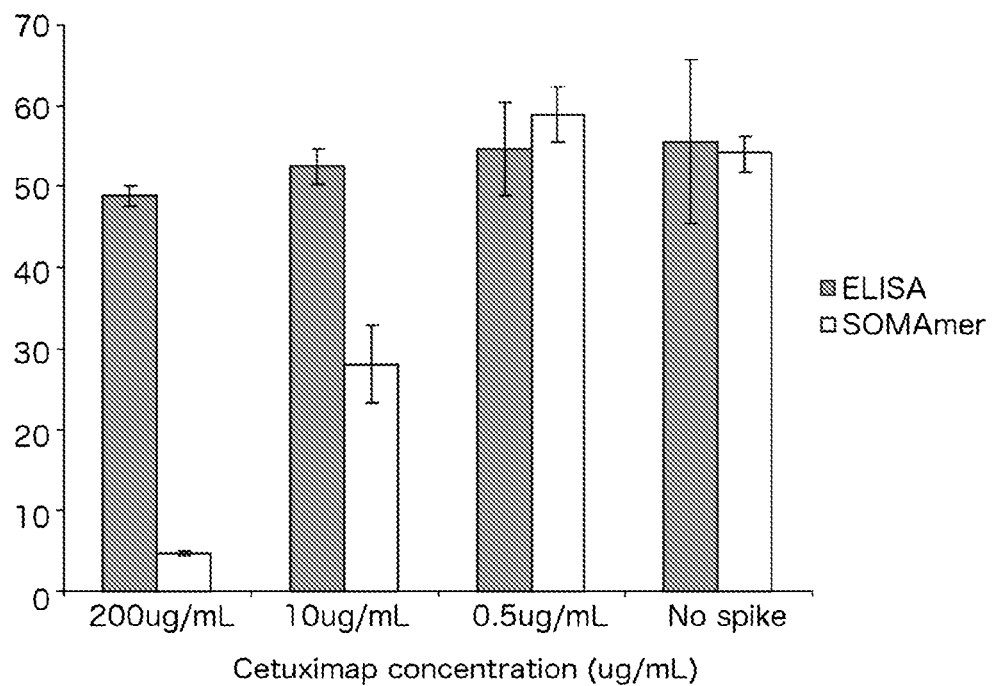
FIG. 9

| Aptamer No. | SEQ ID NO | Copy Number | Alignment | | |
|---|---|---|---|---|---|
| 2677-2224 | 34 | 70 | | GGATTGTTGGATTCTT TAA GTTGG |
| 2677-1664 | 35 | 1 | AG | GAATTGTTGGATTATT TAA GTTGCTGACCGTTTAGGGG |
| 2677-1967 | 36 | 1 | GA GTCGTAGTGGGTCG | GGATTGTTGGATTCTT A GTTAGGTG |
| 2677-736 | 37 | 12 | GA GTTGTATGGGGTC | GGATTGTTGGATTCTT TAA GTTGG |
| 2677-15 | 38 | 1212 | ATCGA GGTTGT GGGTC | GGATTGTTGGATTCTT TAA GTTGG |
| 2677-8925 | 39 | 1 | ATCGAA GGTTAT GGGTC | GGATTGTTGGATTCTT TAA GT GG |
| 2677-4472 | 40 | 1 | ATCGCA GGTTGT TCGGTC | GGATTGTTGGATTCCT TTAA GTTGG |
| 2677-797 | 41 | 1 | ATCGAC GGTTGT GGATCC | GGATTGTTGGACTCTT TA GT G |
| 2677-6391 | 42 | 3 | ATCGA GGTTGT GGGTC | GGATTGTTGGATTTAT TA GGT G |
| 2677-2248 | 43 | 1 | ATCGA GGTTGT GGGTT | GGATTGTTGGATTCTT TAA CT GGT |
| 2677-1013 | 44 | 1 | ATGTCGAGGCTGT GGTC | GGATTGTTGGATTCTT AA GT G |
| 2677-10705 | 45 | 1 | ATCA GG TGT GGTC | GGATTGTGGATTCTT A TTAGGT |
| 2677-9548 | 46 | 1 | CGATCAGTAGGTATT GGTC | GGATTGTGGATTCTT AAAGTTGG |
| 2677-4552 | 47 | 1 | TAC AGCGG | GCATTGTTGGATTCTT TAA GTTACGTAAAGC |
| 2677-515 | 48 | 90 | TGGA TAT GAG | GGATTGTTGGATTCCT TAA GTTGCTCAGAA |
| 2677-7161 | 49 | 1 | TGGA TAT GAG | GCATTGTTGGATTCTT TA GTTGCTCGAA |
| 2677-4341 | 50 | 1 | TGGA CTAT GAG | GATTGTTGGATTCTT AA GTTGCTCAGAA |
| 2677-6782 | 51 | 1 | CTATT GAGT | GCATTGTTAGATTCTT TAA GTTCGGAACCAG |
| 2677-3010 | 52 | 23 | TGGT GT | GGATTGTTAGATTCTT TAA GTTCGCGGGCACCTT |
| 2677-7224 | 53 | 1 | GGACAT | GAATTGTTAGATTCTT TAAAGTTAGTGGTTACTGA |
| 2677-8809 | 54 | 1 | GGGGT | GAATTGTTAGATTCTT TAA GTTCGGGGCGCACCT |

T = 5-(N-benzylcarboxyamido)-2'-deoxyuridine

FIG. 10

| | | | | | | | | | | | | | | | | |
|---|---|---|---|---|---|---|---|---|---|---|---|---|---|---|---|---|
| A | 0 | 0 | 0 | 0 | 9 | 0 | 0 | 5 | 7 | 2 | 2 | 0 | 0 | 0 | 6 | 0 | ↑ |
| C | 0 | 1 | 0 | 0 | 0 | 0 | 8 | 0 | 2 | 1 | 0 | 0 | 2 | 1 | 1 | 1 | 0 |
| G | 0 | 0 | 1 | 3 | 0 | 3 | 4 | 8 | 1 | 1 | 0 | 9 | 11 | 0 | 1 | 10 | 0 |
| T/Z | 0 | 0 | 0 | 9 | 3 | 9 | 0 | 1 | 0 | 1 | 0 | 0 | 0 | 15 | 9 | 5 | 13 |
| Total | 0 | 1 | 1 | 12 | 12 | 12 | 12 | 14 | 10 | 5 | 2 | 9 | 13 | 16 | 17 | 17 | 13 |
| A | 0.00 | 0.00 | 0.00 | 0.00 | 0.43 | 0.00 | 0.00 | 0.24 | 0.33 | 0.10 | 0.10 | 0.00 | 0.00 | 0.00 | 0.29 | 0.05 | 0.00 |
| C | 0.00 | 0.05 | 0.00 | 0.05 | 0.00 | 0.00 | 0.38 | 0.00 | 0.10 | 0.05 | 0.00 | 0.00 | 0.10 | 0.05 | 0.05 | 0.05 | 0.00 |
| G | 0.00 | 0.00 | 0.05 | 0.00 | 0.00 | 0.14 | 0.19 | 0.38 | 0.05 | 0.05 | 0.00 | 0.43 | 0.52 | 0.00 | 0.05 | 0.48 | 0.62 |
| T/Z | 0.00 | 0.00 | 0.00 | 0.14 | 0.14 | 0.43 | 0.00 | 0.05 | 0.00 | 0.05 | 0.00 | 0.00 | 0.00 | 0.71 | 0.43 | 0.24 | 0.62 |
| Total | 0.00 | 0.05 | 0.05 | 0.57 | 0.57 | 0.57 | 0.57 | 0.67 | 0.48 | 0.24 | 0.10 | 0.43 | 0.62 | 0.76 | 0.81 | 0.81 | 0.62 |
| A | 0 | 0 | 0 | 1222 | 0 | 0 | 0 | 94 | 1231 | 2 | 2 | 0 | 0 | 0 | 95 | 1 | 0 |
| C | 0 | 1 | 0 | 0 | 0 | 1 | 1221 | 0 | 2 | 1 | 0 | 0 | 2 | 1 | 1 | 1 | 0 |
| G | 0 | 0 | 1 | 0 | 92 | 1222 | 93 | 1232 | 1 | 1 | 0 | 1222 | 1235 | 0 | 23 | 1256 | 1259 |
| T/Z | 0 | 0 | 0 | 92 | 1222 | 92 | 0 | 1 | 0 | 1 | 0 | 0 | 0 | 1350 | 1233 | 94 | 1259 |
| Total | 0 | 1 | 1 | 1314 | 1314 | 1314 | 1314 | 1327 | 1234 | 5 | 2 | 1222 | 1237 | 1351 | 1352 | 1352 | 1259 |
| A | 0.00 | 0.00 | 0.00 | 0.86 | 0.86 | 0.00 | 0.00 | 0.07 | 0.86 | 0.00 | 0.00 | 0.00 | 0.00 | 0.00 | 0.07 | 0.00 | 0.00 |
| C | 0.00 | 0.00 | 0.00 | 0.00 | 0.00 | 0.00 | 0.86 | 0.86 | 0.00 | 0.00 | 0.00 | 0.00 | 0.00 | 0.00 | 0.00 | 0.00 | 0.00 |
| G | 0.00 | 0.00 | 0.00 | 0.06 | 0.00 | 0.06 | 0.07 | 0.00 | 0.00 | 0.00 | 0.00 | 0.86 | 0.87 | 0.00 | 0.02 | 0.88 | 0.88 |
| T/Z | 0.00 | 0.00 | 0.00 | 0.06 | 0.86 | 0.86 | 0.00 | 0.00 | 0.00 | 0.00 | 0.00 | 0.00 | 0.00 | 0.95 | 0.87 | 0.07 | 0.88 |
| Total | 0.00 | 0.00 | 0.00 | 0.92 | 0.92 | 0.92 | 0.92 | 0.93 | 0.87 | 0.00 | 0.00 | 0.86 | 0.87 | 0.95 | 0.95 | 0.95 | 0.88 |

Z = 5-(N-benzylcarboxyamido)-2'-deoxyuridine

FIG. 11

|   |   |   |   |   |   |   |   |   |   |   |   | G | G | A | Z | Z | G | Z |
|---|---|---|---|---|---|---|---|---|---|---|---|---|---|---|---|---|---|---|
| A | 2 | 1 | 0 | 1 | 5 | 1 | 1 | 0 | 0 | 0 | 21 | 4 | 20 | 0 | 0 | 0 | 0 |
| C | 0 | 0 | 0 | 2 | 0 | 1 | 0 | 10 | 1 | 0 | 0 | 3 | 0 | 0 | 0 | 0 | 0 |
| G | 0 | 1 | 4 | 13 | 14 | 17 | 0 | 0 | 1 | 0 | 0 | 14 | 0 | 0 | 0 | 20 | 1 |
| T/Z | 0 | 1 | 2 | 0 | 0 | 0 | 14 | 2 | 0 | 0 | 0 | 0 | 1 | 21 | 21 | 1 | 20 |
| Total | 2 | 3 | 6 | 16 | 19 | 19 | 15 | 12 | 2 | 0 | 21 | 21 | 21 | 21 | 21 | 21 | 21 |
| A | 0.10 | 0.05 | 0.00 | 0.05 | 0.24 | 0.05 | 0.05 | 0.00 | 0.00 | 0.00 | 1.00 | 0.19 | 0.95 | 0.00 | 0.00 | 0.00 | 0.00 |
| C | 0.00 | 0.00 | 0.00 | 0.10 | 0.00 | 0.05 | 0.00 | 0.48 | 0.05 | 0.00 | 0.00 | 0.14 | 0.00 | 0.00 | 0.00 | 0.00 | 0.00 |
| G | 0.00 | 0.05 | 0.19 | 0.62 | 0.67 | 0.81 | 0.00 | 0.00 | 0.05 | 0.00 | 0.00 | 0.67 | 0.05 | 0.00 | 0.00 | 0.95 | 0.05 |
| T/Z | 0.00 | 0.05 | 0.10 | 0.00 | 0.00 | 0.00 | 0.67 | 0.10 | 0.00 | 0.00 | 0.00 | 0.00 | 0.05 | 1.00 | 1.00 | 0.05 | 0.95 |
| Total | 0.10 | 0.14 | 0.29 | 0.76 | 0.90 | 0.90 | 0.71 | 0.57 | 0.10 | 0.00 | 1.00 | 1.00 | 1.00 | 1.00 | 1.00 | 1.00 | 1.00 |

|   |   |   |   |   |   |   |   |   |   |   |   | G | G | A | Z | Z | G | Z |
|---|---|---|---|---|---|---|---|---|---|---|---|---|---|---|---|---|---|---|
| A | 13 | 1 | 0 | 1 | 94 | 1 | 1 | 0 | 0 | 0 | 1425 | 4 | 1424 | 0 | 0 | 0 | 0 |
| C | 0 | 0 | 0 | 2 | 0 | 0 | 0 | 1234 | 1 | 0 | 0 | 3 | 0 | 0 | 0 | 0 | 0 |
| G | 0 | 1 | 15 | 1326 | 1238 | 1352 | 0 | 0 | 1 | 0 | 0 | 1418 | 0 | 0 | 0 | 1424 | 1 |
| T/Z | 0 | 12 | 2 | 0 | 0 | 0 | 1260 | 2 | 0 | 0 | 0 | 0 | 1 | 1425 | 1425 | 1 | 1424 |
| Total | 13 | 14 | 17 | 1329 | 1332 | 1354 | 1261 | 1236 | 2 | 0 | 1425 | 1425 | 1425 | 1425 | 1425 | 1425 | 1425 |
| A | 0.01 | 0.00 | 0.00 | 0.00 | 0.07 | 0.00 | 0.00 | 0.00 | 0.00 | 0.00 | 1.00 | 0.00 | 1.00 | 0.00 | 0.00 | 0.00 | 0.00 |
| C | 0.00 | 0.00 | 0.00 | 0.00 | 0.00 | 0.00 | 0.00 | 0.87 | 0.00 | 0.00 | 0.00 | 0.00 | 0.00 | 0.00 | 0.00 | 0.00 | 0.00 |
| G | 0.00 | 0.00 | 0.01 | 0.93 | 0.87 | 0.95 | 0.00 | 0.00 | 0.00 | 0.00 | 0.00 | 1.00 | 0.00 | 0.00 | 0.00 | 1.00 | 0.00 |
| T/Z | 0.00 | 0.01 | 0.00 | 0.00 | 0.00 | 0.00 | 0.88 | 0.00 | 0.00 | 0.00 | 0.00 | 0.00 | 0.00 | 1.00 | 1.00 | 0.00 | 1.00 |
| Total | 0.01 | 0.01 | 0.01 | 0.93 | 0.93 | 0.95 | 0.88 | 0.87 | 0.00 | 0.00 | 1.00 | 1.00 | 1.00 | 1.00 | 1.00 | 1.00 | 1.00 |

Z = 5-(N-benzylcarboxyamido)-2′-deoxyuridine

FIG. 11 continued

|       | Z    | G    | G    | A    | Z    | Z    | C    | Z    | Z    |      | (SEQ ID NO: 55) |      |      |      |      |      |      |
|-------|------|------|------|------|------|------|------|------|------|------|------|------|------|------|------|------|------|
| A     | 0    | 4    | 0    | 21   | 0    | 0    | 1    | 1    | 0    | 0    | 0    | 0    | 21   | 16   | 2    | 0    | 0    |
| C     | 0    | 0    | 0    | 0    | 1    | 0    | 19   | 2    | 0    | 0    | 0    | 0    | 0    | 0    | 0    | 1    | 0    |
| G     | 0    | 17   | 21   | 0    | 0    | 0    | 0    | 0    | 0    | 1    | 0    | 0    | 0    | 0    | 1    | 19   | 0    |
| T/Z   | 21   | 0    | 0    | 0    | 20   | 21   | 1    | 18   | 21   | 16   | 0    | 21   | 0    | 0    | 0    | 0    | 21   |
| Total | 21   | 21   | 21   | 21   | 21   | 21   | 21   | 21   | 21   | 16   | 0    | 21   | 21   | 16   | 3    | 20   | 21   |
| A     | 0.00 | 0.19 | 0.00 | 1.00 | 0.00 | 0.00 | 0.05 | 0.05 | 0.00 | 0.00 | 0.00 | 0.00 | 1.00 | 0.76 | 0.10 | 0.00 | 0.00 |
| C     | 0.00 | 0.00 | 0.00 | 0.00 | 0.05 | 0.00 | 0.90 | 0.10 | 0.00 | 0.00 | 0.00 | 0.00 | 0.00 | 0.00 | 0.00 | 0.05 | 0.00 |
| G     | 0.00 | 0.81 | 1.00 | 0.00 | 0.00 | 0.00 | 0.00 | 0.00 | 0.00 | 0.05 | 0.00 | 0.00 | 0.00 | 0.00 | 0.00 | 0.90 | 0.00 |
| T/Z   | 1.00 | 0.00 | 0.00 | 0.00 | 0.95 | 1.00 | 0.05 | 0.86 | 1.00 | 0.76 | 0.00 | 1.00 | 0.00 | 0.00 | 0.00 | 0.00 | 1.00 |
| Total | 1.00 | 1.00 | 1.00 | 1.00 | 1.00 | 1.00 | 1.00 | 1.00 | 1.00 | 0.76 | 0.00 | 1.00 | 1.00 | 0.76 | 0.14 | 0.95 | 1.00 |
|       | Z    | G    | G    | A    | Z    | Z    | C    | Z    | Z    |      |      |      |      |      |      |      |      |
| A     | 0    | 26   | 0    | 1425 | 0    | 0    | 1    | 3    | 0    | 0    | 0    | 0    | 1425 | 1418 | 2    | 0    | 0    |
| C     | 0    | 0    | 0    | 0    | 1    | 0    | 1421 | 2    | 0    | 0    | 0    | 0    | 0    | 0    | 0    | 1    | 0    |
| G     | 0    | 1399 | 1425 | 0    | 0    | 0    | 0    | 0    | 0    | 1    | 0    | 0    | 0    | 0    | 3    | 1423 | 0    |
| T/Z   | 1425 | 0    | 0    | 0    | 1424 | 1425 | 3    | 1420 | 1425 | 1420 | 0    | 1425 | 0    | 0    | 5    | 0    | 1425 |
| Total | 1425 | 1425 | 1425 | 1425 | 1425 | 1425 | 1425 | 1425 | 1425 | 1420 | 0    | 1425 | 1425 | 1418 | 5    | 1424 | 1425 |
| A     | 0.00 | 0.02 | 0.00 | 1.00 | 0.00 | 0.00 | 0.00 | 0.00 | 0.00 | 0.00 | 0.00 | 0.00 | 1.00 | 1.00 | 0.00 | 0.00 | 0.00 |
| C     | 0.00 | 0.00 | 0.00 | 0.00 | 0.00 | 0.00 | 1.00 | 0.00 | 0.00 | 0.00 | 0.00 | 0.00 | 0.00 | 0.00 | 0.00 | 0.00 | 0.00 |
| G     | 0.00 | 0.98 | 1.00 | 0.00 | 0.00 | 0.00 | 0.00 | 0.00 | 0.00 | 0.00 | 0.00 | 0.00 | 0.00 | 0.00 | 0.00 | 1.00 | 0.00 |
| T/Z   | 1.00 | 0.00 | 0.00 | 0.00 | 1.00 | 1.00 | 0.00 | 1.00 | 1.00 | 1.00 | 0.00 | 1.00 | 0.00 | 0.00 | 0.00 | 0.00 | 1.00 |
| Total | 1.00 | 1.00 | 1.00 | 1.00 | 1.00 | 1.00 | 1.00 | 1.00 | 1.00 | 1.00 | 0.00 | 1.00 | 1.00 | 1.00 | 0.00 | 1.00 | 1.00 |

Z = 5-(N-benzylcarboxyamido)-2'-deoxyuridine

FIG. 11 continued

|       |      |      |      |      |      |      |      |      |      |      |      |      |      |      |      |
|-------|------|------|------|------|------|------|------|------|------|------|------|------|------|------|------|
| A     | 0    | 4    | 0    | 0    | 1    | 5    | 2    | 4    | 5    | 1    | 0    | 0    | 0    | 0    | 0    |
| C     | 0    | 3    | 5    | 1    | 3    | 0    | 3    | 3    | 1    | 3    | 2    | 1    | 0    | 0    | 0    |
| G     | 0    | 14   | 13   | 5    | 4    | 5    | 1    | 1    | 2    | 1    | 0    | 1    | 1    | 1    | 1    |
| T/Z   | 16   | 0    | 0    | 6    | 3    | 0    | 1    | 1    | 0    | 1    | 2    | 2    | 0    | 0    | 0    |
| Total | 16   | 21   | 18   | 12   | 11   | 10   | 9    | 9    | 8    | 6    | 4    | 4    | 1    | 1    | 1    |
| A     | 0.00 | 0.19 | 0.00 | 0.00 | 0.05 | 0.24 | 0.10 | 0.19 | 0.24 | 0.05 | 0.00 | 0.00 | 0.00 | 0.00 | 0.00 |
| C     | 0.00 | 0.14 | 0.24 | 0.05 | 0.14 | 0.00 | 0.14 | 0.14 | 0.05 | 0.14 | 0.10 | 0.05 | 0.00 | 0.00 | 0.00 |
| G     | 0.00 | 0.67 | 0.62 | 0.24 | 0.19 | 0.24 | 0.14 | 0.05 | 0.10 | 0.05 | 0.00 | 0.00 | 0.05 | 0.05 | 0.05 |
| T/Z   | 0.76 | 0.00 | 0.00 | 0.29 | 0.14 | 0.00 | 0.05 | 0.05 | 0.00 | 0.05 | 0.19 | 0.19 | 0.00 | 0.00 | 0.00 |
| Total | 0.76 | 1.00 | 0.86 | 0.57 | 0.52 | 0.48 | 0.43 | 0.43 | 0.38 | 0.29 | 0.19 | 0.19 | 0.05 | 0.05 | 0.05 |
| A     | 0    | 4    | 0    | 0    | 1    | 94   | 2    | 93   | 116  | 1    | 0    | 1    | 0    | 0    | 0    |
| C     | 0    | 25   | 94   | 23   | 92   | 0    | 3    | 25   | 1    | 25   | 24   | 1    | 0    | 0    | 0    |
| G     | 0    | 1396 | 1326 | 5    | 26   | 27   | 114  | 1    | 2    | 1    | 0    | 1    | 1    | 1    | 1    |
| T/Z   | 1418 | 0    | 0    | 95   | 3    | 0    | 1    | 1    | 0    | 1    | 2    | 24   | 0    | 0    | 0    |
| Total | 1418 | 1425 | 1420 | 123  | 122  | 121  | 120  | 120  | 119  | 28   | 26   | 26   | 1    | 1    | 1    |
| A     | 0.00 | 0.00 | 0.00 | 0.00 | 0.00 | 0.07 | 0.00 | 0.07 | 0.08 | 0.00 | 0.00 | 0.00 | 0.00 | 0.00 | 0.00 |
| C     | 0.00 | 0.02 | 0.07 | 0.02 | 0.06 | 0.00 | 0.00 | 0.02 | 0.00 | 0.02 | 0.02 | 0.00 | 0.00 | 0.00 | 0.00 |
| G     | 0.00 | 0.98 | 0.93 | 0.00 | 0.02 | 0.02 | 0.08 | 0.00 | 0.00 | 0.00 | 0.00 | 0.00 | 0.00 | 0.00 | 0.00 |
| T/Z   | 1.00 | 0.00 | 0.00 | 0.07 | 0.00 | 0.00 | 0.00 | 0.00 | 0.00 | 0.02 | 0.02 | 0.02 | 0.00 | 0.00 | 0.00 |
| Total | 1.00 | 1.00 | 1.00 | 0.09 | 0.09 | 0.08 | 0.08 | 0.08 | 0.08 | 0.02 | 0.02 | 0.02 | 0.00 | 0.00 | 0.00 |

Z = 5-(N-benzylcarboxyamido)-2'-deoxyuridine

FIG. 11 continued

SEQUENCE LISTING

```
<160> NUMBER OF SEQ ID NOS: 55

<210> SEQ ID NO 1
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is independently, a 5-position modified
      2'-deoxyuridine
<220> FEATURE:
<221> NAME/KEY: misc_feature
<222> LOCATION: (8)..(9)
<223> OTHER INFORMATION: n is independently, a 5-position modified
      2'-deoxyuridine
<220> FEATURE:
<221> NAME/KEY: misc_feature
<222> LOCATION: (11)..(11)
<223> OTHER INFORMATION: n is independently, a 5-position modified
      2'-deoxyuridine
<220> FEATURE:
<221> NAME/KEY: misc_feature
<222> LOCATION: (15)..(15)
<223> OTHER INFORMATION: n is independently, a 5-position modified
      2'-deoxyuridine
<220> FEATURE:
<221> NAME/KEY: misc_feature
<222> LOCATION: (20)..(21)
<223> OTHER INFORMATION: n is independently, a 5-position modified
      2'-deoxyuridine
<220> FEATURE:
<221> NAME/KEY: misc_feature
<222> LOCATION: (23)..(24)
<223> OTHER INFORMATION: n is independently, a 5-position modified
      2'-deoxyuridine
<220> FEATURE:
<221> NAME/KEY: misc_feature
<222> LOCATION: (28)..(29)
<223> OTHER INFORMATION: n is independently, a 5-position modified
      2'-deoxyuridine
<220> FEATURE:
<221> NAME/KEY: misc_feature
<222> LOCATION: (31)..(33)
<223> OTHER INFORMATION: n is a, c, g, or t
<220> FEATURE:
<221> NAME/KEY: misc_feature
<222> LOCATION: (37)..(38)
<223> OTHER INFORMATION: n is independennly, a 5-position modified
      2'-deoxyuridine

<400> SEQUENCE: 1
ancgaggnng ngggncggan ngnnggannc nnnaagnngg gaacaccaac cgagaacg    58
```

```
<210> SEQ ID NO 2
<211> LENGTH: 17
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is independently, a 5-position modified
      2'-deoxyuridine
<220> FEATURE:
<221> NAME/KEY: misc_feature
<222> LOCATION: (4)..(5)
<223> OTHER INFORMATION: n is independently, a 5-position modified
      2'-deoxyuridine
<220> FEATURE:
<221> NAME/KEY: misc_feature
<222> LOCATION: (9)..(10)
<223> OTHER INFORMATION: n is independently, a 5-position modified
      2'-deoxyuridine
<220> FEATURE:
<221> NAME/KEY: misc_feature
<222> LOCATION: (12)..(14)
<223> OTHER INFORMATION: n is independently, a 5-position modified
      2'-deoxyuridine

<400> SEQUENCE: 2
nngnnggann cnnnaag                                                      17

<210> SEQ ID NO 3
<211> LENGTH: 58
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (8)..(9)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (31)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(38)
<223> OTHER INFORMATION: n is 5-(N-benzylcarboxyamido)-2'-deoxyuridine

<400> SEQUENCE: 3
```
ancgaggnng ngggncggan ngnnggannc nnnaagnngg gaacaccaac cgagaacg    58

<210> SEQ ID NO 4
<211> LENGTH: 74
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (18)..(18)
<223> OTHER INFORMATION: n is 5-(N-benzylcarboxyamido)-2'-deoxyuridine
<220> FEATURE:
<221> NAME/KEY: misc_feature
<222> LOCATION: (24)..(25)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (31)..(31)
<223> OTHER INFORMATION: n is 5-(N-benzylcarboxyamido)-2'-deoxyuridine
<220> FEATURE:
<221> NAME/KEY: misc_feature
<222> LOCATION: (36)..(37)
<223> OTHER INFORMATION: n is 5-(N-benzylcarboxyamido)-2'-deoxyuridine
<220> FEATURE:
<221> NAME/KEY: misc_feature
<222> LOCATION: (39)..(40)
<223> OTHER INFORMATION: n is 5-(N-benzylcarboxyamido)-2'-deoxyuridine
<220> FEATURE:
<221> NAME/KEY: misc_feature
<222> LOCATION: (44)..(45)
<223> OTHER INFORMATION: n is 5-(N-benzylcarboxyamido)-2'-deoxyuridine
<220> FEATURE:
<221> NAME/KEY: misc_feature
<222> LOCATION: (47)..(49)
<223> OTHER INFORMATION: n is 5-(N-benzylcarboxyamido)-2'-deoxyuridine
<220> FEATURE:
<221> NAME/KEY: misc_feature
<222> LOCATION: (53)..(54)
<223> OTHER INFORMATION: n is 5-(N-benzylcarboxyamido)-2'-deoxyuridine

<400> SEQUENCE: 4
ccacgcnggg ngggncancg aggnngnggg ncgganngnn gganncnnna agnngggaac    60
accaaccgag aacg    74

<210> SEQ ID NO 5
<211> LENGTH: 50
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is independently, a 5-position modified
      2'-deoxyuridine
<220> FEATURE:
<221> NAME/KEY: misc_feature
<222> LOCATION: (8)..(9)

```
<223> OTHER INFORMATION: n is independently, a 5-position modified
      2'-deoxyuridine
<220> FEATURE:
<221> NAME/KEY: misc_feature
<222> LOCATION: (11)..(11)
<223> OTHER INFORMATION: n is independently, a 5-position modified
      2'-deoxyuridine
<220> FEATURE:
<221> NAME/KEY: misc_feature
<222> LOCATION: (15)..(15)
<223> OTHER INFORMATION: n is independently, a 5-position modified
      2'-deoxyuridine
<220> FEATURE:
<221> NAME/KEY: misc_feature
<222> LOCATION: (20)..(21)
<223> OTHER INFORMATION: n is independently, a 5-position modified
      2'-deoxyuridine
<220> FEATURE:
<221> NAME/KEY: misc_feature
<222> LOCATION: (23)..(24)
<223> OTHER INFORMATION: n is independently, a 5-position modified
      2'-deoxyuridine
<220> FEATURE:
<221> NAME/KEY: misc_feature
<222> LOCATION: (28)..(29)
<223> OTHER INFORMATION: n is independently, a 5-position modified
      2'-deoxyuridine
<220> FEATURE:
<221> NAME/KEY: misc_feature
<222> LOCATION: (31)..(33)
<223> OTHER INFORMATION: n is independently, a 5-position modified
      2'-deoxyuridine
<220> FEATURE:
<221> NAME/KEY: misc_feature
<222> LOCATION: (37)..(38)
<223> OTHER INFORMATION: n is independently, a 5-position modified
      2'-deoxyuridine

<400> SEQUENCE: 5
ancgaggnng ngggncggan ngnnggannc nnnaagnngg gaacaccaac              50

<210> SEQ ID NO 6
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is independently, a 5-position modified
      2'-deoxyuridine
<220> FEATURE:
<221> NAME/KEY: misc_feature
<222> LOCATION: (8)..(9)
<223> OTHER INFORMATION: n is independently, a 5-position modified
      2'-deoxyuridine
<220> FEATURE:
<221> NAME/KEY: misc_feature
<222> LOCATION: (11)..(11)
<223> OTHER INFORMATION: n is independently, a 5-position modified
      2'-deoxyuridine
<220> FEATURE:
<221> NAME/KEY: misc_feature
<222> LOCATION: (15)..(15)
<223> OTHER INFORMATION: n is independently, a 5-position modified
      2'-deoxyuridine
<220> FEATURE:
<221> NAME/KEY: misc_feature
<222> LOCATION: (20)..(21)
<223> OTHER INFORMATION: n is independently, a 5-position modified
      2'-deoxyuridine
<220> FEATURE:
<221> NAME/KEY: misc_feature
<222> LOCATION: (23)..(24)
<223> OTHER INFORMATION: n is independently, a 5-position modified
      2'-deoxyuridine
```

```
<220> FEATURE:
<221> NAME/KEY: misc_feature
<222> LOCATION: (28)..(29)
<223> OTHER INFORMATION: n is independently, a 5-position modified
      2'-deoxyuridine
<220> FEATURE:
<221> NAME/KEY: misc_feature
<222> LOCATION: (31)..(33)
<223> OTHER INFORMATION: n is independently, a 5-position modified
      2'-deoxyuridine
<220> FEATURE:
<221> NAME/KEY: misc_feature
<222> LOCATION: (37)..(38)
<223> OTHER INFORMATION: n is independently, a 5-position modified
      2'-deoxyuridine

<400> SEQUENCE: 6
ancgaggnng ngggncggan ngnnggannc nnnaagnngg                              40

<210> SEQ ID NO 7
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(5)
<223> OTHER INFORMATION: n is independently, a 5-position modified
      2'-deoxyuridine
<220> FEATURE:
<221> NAME/KEY: misc_feature
<222> LOCATION: (7)..(7)
<223> OTHER INFORMATION: n is independently, a 5-position modified
      2'-deoxyuridine
<220> FEATURE:
<221> NAME/KEY: misc_feature
<222> LOCATION: (9)..(9)
<223> OTHER INFORMATION: n is independently, a 5-position modified
      2'-deoxyuridine
<220> FEATURE:
<221> NAME/KEY: misc_feature
<222> LOCATION: (14)..(14)
<223> OTHER INFORMATION: n is independently, a 5-position modified
      2'-deoxyuridine
<220> FEATURE:
<221> NAME/KEY: misc_feature
<222> LOCATION: (19)..(20)
<223> OTHER INFORMATION: n is independently, a 5-position modified
      2'-deoxyuridine
<220> FEATURE:
<221> NAME/KEY: misc_feature
<222> LOCATION: (22)..(23)
<223> OTHER INFORMATION: n is independently, a 5-position modified
      2'-deoxyuridine
<220> FEATURE:
<221> NAME/KEY: misc_feature
<222> LOCATION: (27)..(28)
<223> OTHER INFORMATION: n is independently, a 5-position modified
      2'-deoxyuridine
<220> FEATURE:
<221> NAME/KEY: misc_feature
<222> LOCATION: (30)..(32)
<223> OTHER INFORMATION: n is independently, a 5-position modified
      2'-deoxyuridine
<220> FEATURE:
<221> NAME/KEY: misc_feature
<222> LOCATION: (36)..(37)
<223> OTHER INFORMATION: n is independently, a 5-position modified
      2'-deoxyuridine

<400> SEQUENCE: 7
gagnngnang gggncggann gnngganncn nnaagnncgg                              40

<210> SEQ ID NO 8
```

```
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is independently, a 5-position modified
      2'-deoxyuridine
<220> FEATURE:
<221> NAME/KEY: misc_feature
<222> LOCATION: (9)..(10)
<223> OTHER INFORMATION: n is independently, a 5-position modified
      2'-deoxyuridine
<220> FEATURE:
<221> NAME/KEY: misc_feature
<222> LOCATION: (12)..(13)
<223> OTHER INFORMATION: n is independently, a 5-position modified
      2'-deoxyuridine
<220> FEATURE:
<221> NAME/KEY: misc_feature
<222> LOCATION: (17)..(18)
<223> OTHER INFORMATION: n is independently, a 5-position modified
      2'-deoxyuridine
<220> FEATURE:
<221> NAME/KEY: misc_feature
<222> LOCATION: (20)..(22)
<223> OTHER INFORMATION: n is independently, a 5-position modified
      2'-deoxyuridine
<220> FEATURE:
<221> NAME/KEY: misc_feature
<222> LOCATION: (26)..(27)
<223> OTHER INFORMATION: n is independently, a 5-position modified
      2'-deoxyuridine

<400> SEQUENCE: 8
gggncggann gnngganncn nnaagnn                                              27

<210> SEQ ID NO 9
<211> LENGTH: 73
<212> TYPE: DNA
<213> ORGANISM: Artificial Sequence
<220> FEATURE:
<223> OTHER INFORMATION: synthetic

<400> SEQUENCE: 9
cacgctgggt gggtcatcga ggttgtgggt cggattgttg gattctttaa gttgggaaca         60
ccaaccgaga acg                                                            73

<210> SEQ ID NO 10
<211> LENGTH: 74
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: n is 5-(N-benzylcarboxyamido)-2'-deoxyuridine
<220> FEATURE:
<221> NAME/KEY: misc_feature
<222> LOCATION: (24)..(25)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (31)..(31)
<223> OTHER INFORMATION: n is 5-(N-benzylcarboxyamido)-2'-deoxyuridine
<220> FEATURE:
<221> NAME/KEY: misc_feature
```

<222> LOCATION: (36)..(37)
<223> OTHER INFORMATION: n is 5-(N-benzylcarboxyamido)-2'-deoxyuridine
<220> FEATURE:
<221> NAME/KEY: misc_feature
<222> LOCATION: (39)..(40)
<223> OTHER INFORMATION: n is 5-(N-benzylcarboxyamido)-2'-deoxyuridine
<220> FEATURE:
<221> NAME/KEY: misc_feature
<222> LOCATION: (44)..(45)
<223> OTHER INFORMATION: n is 5-(N-benzylcarboxyamido)-2'-deoxyuridine
<220> FEATURE:
<221> NAME/KEY: misc_feature
<222> LOCATION: (47)..(49)
<223> OTHER INFORMATION: n is 5-(N-benzylcarboxyamido)-2'-deoxyuridine
<220> FEATURE:
<221> NAME/KEY: misc_feature
<222> LOCATION: (53)..(54)
<223> OTHER INFORMATION: n is 5-(N-benzylcarboxyamido)-2'-deoxyuridine

<400> SEQUENCE: 10
ccacgctggg tgggtcancg aggnngnggg ncggannngnn ggannncnnna agnngggaac        60 accaaccgag aacg        74

<210> SEQ ID NO 11
<211> LENGTH: 50
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (13)..(14)
<223> OTHER INFORMATION: n is 5-(N-benzylcarboxyamido)-2'-deoxyuridine
<220> FEATURE:
<221> NAME/KEY: misc_feature
<222> LOCATION: (16)..(16)
<223> OTHER INFORMATION: n is 5-(N-benzylcarboxyamido)-2'-deoxyuridine
<220> FEATURE:
<221> NAME/KEY: misc_feature
<222> LOCATION: (20)..(20)
<223> OTHER INFORMATION: n is 5-(N-benzylcarboxyamido)-2'-deoxyuridine
<220> FEATURE:
<221> NAME/KEY: misc_feature
<222> LOCATION: (25)..(26)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (33)..(34)
<223> OTHER INFORMATION: n is 5-(N-benzylcarboxyamido)-2'-deoxyuridine
<220> FEATURE:
<221> NAME/KEY: misc_feature
<222> LOCATION: (36)..(38)
<223> OTHER INFORMATION: n is 5-(N-benzylcarboxyamido)-2'-deoxyuridine
<220> FEATURE:
<221> NAME/KEY: misc_feature
<222> LOCATION: (42)..(43)
<223> OTHER INFORMATION: n is 5-(N-benzylcarboxyamido)-2'-deoxyuridine

<400> SEQUENCE: 11
gggtcancga ggnngngggn cggannngnng ganncnnnaa gnngggaaca        50

<210> SEQ ID NO 12
<211> LENGTH: 50
<212> TYPE: DNA
<213> ORGANISM: Artificial Sequence
<220> FEATURE:

```
<223> OTHER INFORMATION: synthetic
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (21)..(21)
<223> OTHER INFORMATION: n is 5-(N-benzylcarboxyamido)-2'-deoxyuridine
<220> FEATURE:
<221> NAME/KEY: misc_feature
<222> LOCATION: (25)..(25)
<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine
<220> FEATURE:
<221> NAME/KEY: misc_feature
<222> LOCATION: (33)..(34)
<223> OTHER INFORMATION: n is 5-(N-benzylcarboxyamido)-2'-deoxyuridine
<220> FEATURE:
<221> NAME/KEY: misc_feature
<222> LOCATION: (38)..(39)
<223> OTHER INFORMATION: n is 5-(N-benzylcarboxyamido)-2'-deoxyuridine
<220> FEATURE:
<221> NAME/KEY: misc_feature
<222> LOCATION: (41)..(43)
<223> OTHER INFORMATION: n is 5-(N-benzylcarboxyamido)-2'-deoxyuridine
<220> FEATURE:
<221> NAME/KEY: misc_feature
<222> LOCATION: (47)..(48)
<223> OTHER INFORMATION: n is 5-(N-benzylcarboxyamido)-2'-deoxyuridine

<400> SEQUENCE: 12
tgggtgggtc ancgaggnng ngggncggan ngnnggannc nnnaagnngg         50

<210> SEQ ID NO 13
<211> LENGTH: 50
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (8)..(9)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
```

```
<222> LOCATION: (31)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(38)
<223> OTHER INFORMATION: n is 5-(N-benzylcarboxyamido)-2'-deoxyuridine

<400> SEQUENCE: 13
ancgaggnng ngggncggan ngnnggannc nnnaagnngg gaacaccaac                50

<210> SEQ ID NO 14
<211> LENGTH: 55
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (21)..(21)
<223> OTHER INFORMATION: n is 5-(N-benzylcarboxyamido)-2'-deoxyuridine
<220> FEATURE:
<221> NAME/KEY: misc_feature
<222> LOCATION: (25)..(25)
<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine
<220> FEATURE:
<221> NAME/KEY: misc_feature
<222> LOCATION: (33)..(34)
<223> OTHER INFORMATION: n is 5-(N-benzylcarboxyamido)-2'-deoxyuridine
<220> FEATURE:
<221> NAME/KEY: misc_feature
<222> LOCATION: (38)..(39)
<223> OTHER INFORMATION: n is 5-(N-benzylcarboxyamido)-2'-deoxyuridine
<220> FEATURE:
<221> NAME/KEY: misc_feature
<222> LOCATION: (41)..(43)
<223> OTHER INFORMATION: n is 5-(N-benzylcarboxyamido)-2'-deoxyuridine
<220> FEATURE:
<221> NAME/KEY: misc_feature
<222> LOCATION: (47)..(48)
<223> OTHER INFORMATION: n is 5-(N-benzylcarboxyamido)-2'-deoxyuridine

<400> SEQUENCE: 14
tgggtgggtc ancgaggnng ngggncggan ngnnggannc nnnaagnngg gaaca           55

<210> SEQ ID NO 15
<211> LENGTH: 55
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (13)..(14)
<223> OTHER INFORMATION: n is 5-(N-benzylcarboxyamido)-2'-deoxyuridine
<220> FEATURE:
<221> NAME/KEY: misc_feature
<222> LOCATION: (16)..(16)
<223> OTHER INFORMATION: n is 5-(N-benzylcarboxyamido)-2'-deoxyuridine
<220> FEATURE:
```

```
<221> NAME/KEY: misc_feature
<222> LOCATION: (20)..(20)
<223> OTHER INFORMATION: n is 5-(N-benzylcarboxyamido)-2'-deoxyuridine
<220> FEATURE:
<221> NAME/KEY: misc_feature
<222> LOCATION: (25)..(26)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (33)..(34)
<223> OTHER INFORMATION: n is 5-(N-benzylcarboxyamido)-2'-deoxyuridine
<220> FEATURE:
<221> NAME/KEY: misc_feature
<222> LOCATION: (36)..(38)
<223> OTHER INFORMATION: n is 5-(N-benzylcarboxyamido)-2'-deoxyuridine
<220> FEATURE:
<221> NAME/KEY: misc_feature
<222> LOCATION: (42)..(43)
<223> OTHER INFORMATION: n is 5-(N-benzylcarboxyamido)-2'-deoxyuridine

<400> SEQUENCE: 15
gggtcancga ggnngngggn cgganngnng gannennnaa gnngggaaca ccaac         55

<210> SEQ ID NO 16
<211> LENGTH: 68
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 16
gctgggtggg tcancgaggn ngnggncgg anngnnggan ncnnnaagnn gggaacacca    60
accgagaa                                                           68
```

```
<210> SEQ ID NO 17
<211> LENGTH: 66
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 17
gctgggtggg tcancgaggn ngnggncgg anngnnggan ncnnaagnn gggaacacca      60 accgag                                                              66

<210> SEQ ID NO 18
<211> LENGTH: 64
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
```

```
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 18
gctgggtggg tcancgaggn ngnggncgg anngnnggan ncnnnaagnn gggaacacca      60
accg                                                                 64

<210> SEQ ID NO 19
<211> LENGTH: 62
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 19
gctgggtggg tcancgaggn ngnggncgg anngnnggan ncnnnaagnn gggaacacca      60
ac                                                                   62

<210> SEQ ID NO 20
<211> LENGTH: 60
<212> TYPE: DNA
<213> ORGANISM: Artificial Sequence
<220> FEATURE:
<223> OTHER INFORMATION: synthetic
<220> FEATURE:
<221> NAME/KEY: misc_feature
```

```
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 20
gctgggtggg tcancgaggn ngngggncgg anngnnggan ncnnnaagnn gggaacacca          60

<210> SEQ ID NO 21
<211> LENGTH: 58
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
```

```
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 21
gctgggtggg tcancgaggn ngnggggncgg anngnnggan ncnnnaagnn gggaacac      58

<210> SEQ ID NO 22
<211> LENGTH: 56
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 22
gctgggtggg tcancgaggn ngnggggncgg anngnnggan ncnnnaagnn gggaac        56

<210> SEQ ID NO 23
<211> LENGTH: 54
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
```

```
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 23
gctgggtggg tcancgaggn ngngggncgg anngnnggan ncnnnaagnn ggga            54

<210> SEQ ID NO 24
<211> LENGTH: 52
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 24
gctgggtggg tcancgaggn ngngggncgg anngnnggan ncnnnaagnn gg              52

<210> SEQ ID NO 25
<211> LENGTH: 50
<212> TYPE: DNA
<213> ORGANISM: Artificial Sequence
<220> FEATURE:
```

```
<223> OTHER INFORMATION: synthetic
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine
<220> FEATURE:
<221> NAME/KEY: misc_feature
<222> LOCATION: (43)..(45)
<223> OTHER INFORMATION: n is 5-(N-benzylcarboxyamido)-2'-deoxyuridine
<220> FEATURE:
<221> NAME/KEY: misc_feature
<222> LOCATION: (49)..(50)
<223> OTHER INFORMATION: n is 5-(N-benzylcarboxyamido)-2'-deoxyuridine

<400> SEQUENCE: 25
gctgggtggg tcancgaggn ngngggncgg anngnnggan ncnnnaagnn            50

<210> SEQ ID NO 26
<211> LENGTH: 64
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (21)..(21)
<223> OTHER INFORMATION: n is 5-(N-benzylcarboxyamido)-2'-deoxyuridine
<220> FEATURE:
<221> NAME/KEY: misc_feature
<222> LOCATION: (25)..(25)
<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine
<220> FEATURE:
<221> NAME/KEY: misc_feature
<222> LOCATION: (33)..(34)
<223> OTHER INFORMATION: n is 5-(N-benzylcarboxyamido)-2'-deoxyuridine
<220> FEATURE:
<221> NAME/KEY: misc_feature
<222> LOCATION: (38)..(39)
<223> OTHER INFORMATION: n is 5-(N-benzylcarboxyamido)-2'-deoxyuridine
<220> FEATURE:
<221> NAME/KEY: misc_feature
```

<222> LOCATION: (41)..(43)
<223> OTHER INFORMATION: n is 5-(N-benzylcarboxamido)-2'-deoxyuridine
<220> FEATURE:
<221> NAME/KEY: misc_feature
<222> LOCATION: (47)..(48)
<223> OTHER INFORMATION: n is 5-(N-benzylcarboxamido)-2'-deoxyuridine

<400> SEQUENCE: 26
tgggtgggtc ancgaggnng ngggncggan ngnnggannc nnnaagnngg gaacaccaac   60
cgag   64

<210> SEQ ID NO 27
<211> LENGTH: 62
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: n is 5-(N-benzylcarboxamido)-2'-deoxyuridine
<220> FEATURE:
<221> NAME/KEY: misc_feature
<222> LOCATION: (16)..(17)
<223> OTHER INFORMATION: n is 5-(N-benzylcarboxamido)-2'-deoxyuridine
<220> FEATURE:
<221> NAME/KEY: misc_feature
<222> LOCATION: (19)..(19)
<223> OTHER INFORMATION: n is 5-(N-benzylcarboxamido)-2'-deoxyuridine
<220> FEATURE:
<221> NAME/KEY: misc_feature
<222> LOCATION: (23)..(23)
<223> OTHER INFORMATION: n is 5-(N-benzylcarboxamido)-2'-deoxyuridine
<220> FEATURE:
<221> NAME/KEY: misc_feature
<222> LOCATION: (28)..(29)
<223> OTHER INFORMATION: n is 5-(N-benzylcarboxamido)-2'-deoxyuridine
<220> FEATURE:
<221> NAME/KEY: misc_feature
<222> LOCATION: (31)..(32)
<223> OTHER INFORMATION: n is 5-(N-benzylcarboxamido)-2'-deoxyuridine
<220> FEATURE:
<221> NAME/KEY: misc_feature
<222> LOCATION: (36)..(37)
<223> OTHER INFORMATION: n is 5-(N-benzylcarboxamido)-2'-deoxyuridine
<220> FEATURE:
<221> NAME/KEY: misc_feature
<222> LOCATION: (39)..(41)
<223> OTHER INFORMATION: n is 5-(N-benzylcarboxamido)-2'-deoxyuridine
<220> FEATURE:
<221> NAME/KEY: misc_feature
<222> LOCATION: (45)..(46)
<223> OTHER INFORMATION: n is 5-(N-benzylcarboxamido)-2'-deoxyuridine

<400> SEQUENCE: 27
ggtgggtcan cgaggnngng ggncgganng nngganncnn naagnnggga acaccaaccg   60
ag   62

<210> SEQ ID NO 28
<211> LENGTH: 60
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: n is 5-(N-benzylcarboxamido)-2'-deoxyuridine
<220> FEATURE:
<221> NAME/KEY: misc_feature
<222> LOCATION: (14)..(15)
<223> OTHER INFORMATION: n is 5-(N-benzylcarboxamido)-2'-deoxyuridine
<220> FEATURE:

```
<221> NAME/KEY: misc_feature
<222> LOCATION: (17)..(17)
<223> OTHER INFORMATION: n is 5-(N-benzylcarboxyamido)-2'-deoxyuridine
<220> FEATURE:
<221> NAME/KEY: misc_feature
<222> LOCATION: (21)..(21)
<223> OTHER INFORMATION: n is 5-(N-benzylcarboxyamido)-2'-deoxyuridine
<220> FEATURE:
<221> NAME/KEY: misc_feature
<222> LOCATION: (26)..(27)
<223> OTHER INFORMATION: n is 5-(N-benzylcarboxyamido)-2'-deoxyuridine
<220> FEATURE:
<221> NAME/KEY: misc_feature
<222> LOCATION: (29)..(30)
<223> OTHER INFORMATION: n is 5-(N-benzylcarboxyamido)-2'-deoxyuridine
<220> FEATURE:
<221> NAME/KEY: misc_feature
<222> LOCATION: (34)..(35)
<223> OTHER INFORMATION: n is 5-(N-benzylcarboxyamido)-2'-deoxyuridine
<220> FEATURE:
<221> NAME/KEY: misc_feature
<222> LOCATION: (37)..(39)
<223> OTHER INFORMATION: n is 5-(N-benzylcarboxyamido)-2'-deoxyuridine
<220> FEATURE:
<221> NAME/KEY: misc_feature
<222> LOCATION: (43)..(44)
<223> OTHER INFORMATION: n is 5-(N-benzylcarboxyamido)-2'-deoxyuridine

<400> SEQUENCE: 28
tgggtcancg aggnngnggg ncgganngnn ggannncnnna agnngggaac accaaccgag      60

<210> SEQ ID NO 29
<211> LENGTH: 58
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is 5-(N-benzylcarboxyamido)-2'-deoxyuridine
<220> FEATURE:
<221> NAME/KEY: misc_feature
<222> LOCATION: (12)..(13)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (19)..(19)
<223> OTHER INFORMATION: n is 5-(N-benzylcarboxyamido)-2'-deoxyuridine
<220> FEATURE:
<221> NAME/KEY: misc_feature
<222> LOCATION: (24)..(25)
<223> OTHER INFORMATION: n is 5-(N-benzylcarboxyamido)-2'-deoxyuridine
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (35)..(37)
<223> OTHER INFORMATION: n is 5-(N-benzylcarboxyamido)-2'-deoxyuridine
<220> FEATURE:
<221> NAME/KEY: misc_feature
<222> LOCATION: (41)..(42)
<223> OTHER INFORMATION: n is 5-(N-benzylcarboxyamido)-2'-deoxyuridine

<400> SEQUENCE: 29
ggtcancgag gnngngggnc ggannngnngg anncnnnaag nngggaacac caaccgag       58
```

```
<210> SEQ ID NO 30
<211> LENGTH: 56
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is 5-(N-benzylcarboxyamido)-2'-deoxyuridine
<220> FEATURE:
<221> NAME/KEY: misc_feature
<222> LOCATION: (10)..(11)
<223> OTHER INFORMATION: n is 5-(N-benzylcarboxyamido)-2'-deoxyuridine
<220> FEATURE:
<221> NAME/KEY: misc_feature
<222> LOCATION: (13)..(13)
<223> OTHER INFORMATION: n is 5-(N-benzylcarboxyamido)-2'-deoxyuridine
<220> FEATURE:
<221> NAME/KEY: misc_feature
<222> LOCATION: (17)..(17)
<223> OTHER INFORMATION: n is 5-(N-benzylcarboxyamido)-2'-deoxyuridine
<220> FEATURE:
<221> NAME/KEY: misc_feature
<222> LOCATION: (22)..(23)
<223> OTHER INFORMATION: n is 5-(N-benzylcarboxyamido)-2'-deoxyuridine
<220> FEATURE:
<221> NAME/KEY: misc_feature
<222> LOCATION: (25)..(26)
<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine
<220> FEATURE:
<221> NAME/KEY: misc_feature
<222> LOCATION: (33)..(35)
<223> OTHER INFORMATION: n is 5-(N-benzylcarboxyamido)-2'-deoxyuridine
<220> FEATURE:
<221> NAME/KEY: misc_feature
<222> LOCATION: (39)..(40)
<223> OTHER INFORMATION: n is 5-(N-benzylcarboxyamido)-2'-deoxyuridine

<400> SEQUENCE: 30
tcancgaggn ngngggncgg anngnnggan ncnnnaagnn gggaacacca accgag      56

<210> SEQ ID NO 31
<211> LENGTH: 54
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (8)..(9)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
```

```
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (31)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(38)
<223> OTHER INFORMATION: n is 5-(N-benzylcarboxyamido)-2'-deoxyuridine

<400> SEQUENCE: 31
ancgaggnng ngggncggan ngnnggannc nnnaagnngg gaacaccaac cgag         54

<210> SEQ ID NO 32
<211> LENGTH: 52
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is 5-(N-benzylcarboxyamido)-2'-deoxyuridine
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is 5-(N-benzylcarboxyamido)-2'-deoxyuridine
<220> FEATURE:
<221> NAME/KEY: misc_feature
<222> LOCATION: (13)..(13)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (21)..(22)
<223> OTHER INFORMATION: n is 5-(N-benzylcarboxyamido)-2'-deoxyuridine
<220> FEATURE:
<221> NAME/KEY: misc_feature
<222> LOCATION: (26)..(27)
<223> OTHER INFORMATION: n is 5-(N-benzylcarboxyamido)-2'-deoxyuridine
<220> FEATURE:
<221> NAME/KEY: misc_feature
<222> LOCATION: (29)..(31)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine

<400> SEQUENCE: 32
cgaggnngng ggncgganng nnggannnn naagnnggga acaccaaccg ag             52

<210> SEQ ID NO 33
<211> LENGTH: 50
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(5)
<223> OTHER INFORMATION: n is 5-(N-benzylcarboxyamido)-2'-deoxyuridine
<220> FEATURE:
<221> NAME/KEY: misc_feature
```

```
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (16)..(17)
<223> OTHER INFORMATION: n is 5-(N-benzylcarboxyamido)-2'-deoxyuridine
<220> FEATURE:
<221> NAME/KEY: misc_feature
<222> LOCATION: (19)..(20)
<223> OTHER INFORMATION: n is 5-(N-benzylcarboxyamido)-2'-deoxyuridine
<220> FEATURE:
<221> NAME/KEY: misc_feature
<222> LOCATION: (24)..(25)
<223> OTHER INFORMATION: n is 5-(N-benzylcarboxyamido)-2'-deoxyuridine
<220> FEATURE:
<221> NAME/KEY: misc_feature
<222> LOCATION: (27)..(29)
<223> OTHER INFORMATION: n is 5-(N-benzylcarboxyamido)-2'-deoxyuridine
<220> FEATURE:
<221> NAME/KEY: misc_feature
<222> LOCATION: (33)..(34)
<223> OTHER INFORMATION: n is 5-(N-benzylcarboxyamido)-2'-deoxyuridine

<400> SEQUENCE: 33
aggnngnggg ncgganngnn ggannncnnna agnngggaac accaaccgag          50

<210> SEQ ID NO 34
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(5)
<223> OTHER INFORMATION: n is 5-(N-benzylcarboxyamido)-2'-deoxyuridine
<220> FEATURE:
<221> NAME/KEY: misc_feature
<222> LOCATION: (7)..(8)
<223> OTHER INFORMATION: n is 5-(N-benzylcarboxyamido)-2'-deoxyuridine
<220> FEATURE:
<221> NAME/KEY: misc_feature
<222> LOCATION: (12)..(13)
<223> OTHER INFORMATION: n is 5-(N-benzylcarboxyamido)-2'-deoxyuridine
<220> FEATURE:
<221> NAME/KEY: misc_feature
<222> LOCATION: (15)..(17)
<223> OTHER INFORMATION: n is 5-(N-benzylcarboxyamido)-2'-deoxyuridine
<220> FEATURE:
<221> NAME/KEY: misc_feature
<222> LOCATION: (21)..(22)
<223> OTHER INFORMATION: n is 5-(N-benzylcarboxyamido)-2'-deoxyuridine

<400> SEQUENCE: 34
gganngnngg anncnnnaag nngg                                       24

<210> SEQ ID NO 35
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(7)
<223> OTHER INFORMATION: n is 5-(N-benzylcarboxyamido)-2'-deoxyuridine
<220> FEATURE:
<221> NAME/KEY: misc_feature
<222> LOCATION: (9)..(10)
<223> OTHER INFORMATION: n is 5-(N-benzylcarboxyamido)-2'-deoxyuridine
<220> FEATURE:
```

```
<221> NAME/KEY: misc_feature
<222> LOCATION: (14)..(15)
<223> OTHER INFORMATION: n is 5-(N-benzylcarboxyamido)-2'-deoxyuridine
<220> FEATURE:
<221> NAME/KEY: misc_feature
<222> LOCATION: (17)..(19)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (33)..(35)
<223> OTHER INFORMATION: n is 5-(N-benzylcarboxyamido)-2'-deoxyuridine

<400> SEQUENCE: 35
aggaanngnn ggannannna agnngcngac cgnnnagggg                              40

<210> SEQ ID NO 36
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is 5-(N-benzylcarboxyamido)-2'-deoxyuridine
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (10)..(10)
<223> OTHER INFORMATION: n is 5-(N-benzylcarboxyamido)-2'-deoxyuridine
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (31)..(32)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(40)
<223> OTHER INFORMATION: n is 5-(N-benzylcarboxyamido)-2'-deoxyuridine

<400> SEQUENCE: 36
gagncgnagn gggncgggan ngnnggannc nnagnnaggn g                            41

<210> SEQ ID NO 37
<211> LENGTH: 39
```

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(5)
<223> OTHER INFORMATION: n is 5-(N-benzylcarboxyamido)-2'-deoxyuridine
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (9)..(9)
<223> OTHER INFORMATION: n is 5-(N-benzylcarboxyamido)-2'-deoxyuridine
<220> FEATURE:
<221> NAME/KEY: misc_feature
<222> LOCATION: (14)..(14)
<223> OTHER INFORMATION: n is 5-(N-benzylcarboxyamido)-2'-deoxyuridine
<220> FEATURE:
<221> NAME/KEY: misc_feature
<222> LOCATION: (19)..(20)
<223> OTHER INFORMATION: n is 5-(N-benzylcarboxyamido)-2'-deoxyuridine
<220> FEATURE:
<221> NAME/KEY: misc_feature
<222> LOCATION: (22)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(28)
<223> OTHER INFORMATION: n is 5-(N-benzylcarboxyamido)-2'-deoxyuridine
<220> FEATURE:
<221> NAME/KEY: misc_feature
<222> LOCATION: (30)..(32)
<223> OTHER INFORMATION: n is 5-(N-benzylcarboxyamido)-2'-deoxyuridine
<220> FEATURE:
<221> NAME/KEY: misc_feature
<222> LOCATION: (36)..(37)
<223> OTHER INFORMATION: n is 5-(N-benzylcarboxyamido)-2'-deoxyuridine

<400> SEQUENCE: 37
gagnngnang gggncggann gnnggann nnaagnngg                                 39

<210> SEQ ID NO 38
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (8)..(9)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
```

```
<223> OTHER INFORMATION: n is 5-(N-benzylcarboxyamido)-2'-deoxyuridine
<220> FEATURE:
<221> NAME/KEY: misc_feature
<222> LOCATION: (31)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(38)
<223> OTHER INFORMATION: n is 5-(N-benzylcarboxyamido)-2'-deoxyuridine

<400> SEQUENCE: 38
ancgaggnng ngggncggan ngnnggannc nnnaagnngg                    40

<210> SEQ ID NO 39
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (9)..(10)
<223> OTHER INFORMATION: n is 5-(N-benzylcarboxyamido)-2'-deoxyuridine
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (16)..(16)
<223> OTHER INFORMATION: n is 5-(N-benzylcarboxyamido)-2'-deoxyuridine
<220> FEATURE:
<221> NAME/KEY: misc_feature
<222> LOCATION: (21)..(22)
<223> OTHER INFORMATION: n is 5-(N-benzylcarboxyamido)-2'-deoxyuridine
<220> FEATURE:
<221> NAME/KEY: misc_feature
<222> LOCATION: (24)..(25)
<223> OTHER INFORMATION: n is 5-(N-benzylcarboxyamido)-2'-deoxyuridine
<220> FEATURE:
<221> NAME/KEY: misc_feature
<222> LOCATION: (29)..(30)
<223> OTHER INFORMATION: n is 5-(N-benzylcarboxyamido)-2'-deoxyuridine
<220> FEATURE:
<221> NAME/KEY: misc_feature
<222> LOCATION: (32)..(34)
<223> OTHER INFORMATION: n is 5-(N-benzylcarboxyamido)-2'-deoxyuridine
<220> FEATURE:
<221> NAME/KEY: misc_feature
<222> LOCATION: (38)..(38)
<223> OTHER INFORMATION: n is 5-(N-benzylcarboxyamido)-2'-deoxyuridine

<400> SEQUENCE: 39
ancgaaggnn angggncgga nngnnggann cnnnaagngg                    40

<210> SEQ ID NO 40
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (9)..(10)
<223> OTHER INFORMATION: n is 5-(N-benzylcarboxyamido)-2'-deoxyuridine
<220> FEATURE:
<221> NAME/KEY: misc_feature
```

```
<222> LOCATION: (12)..(13)
<223> OTHER INFORMATION: n is 5-(N-benzylcarboxyamido)-2'-deoxyuridine
<220> FEATURE:
<221> NAME/KEY: misc_feature
<222> LOCATION: (17)..(17)
<223> OTHER INFORMATION: n is 5-(N-benzylcarboxyamido)-2'-deoxyuridine
<220> FEATURE:
<221> NAME/KEY: misc_feature
<222> LOCATION: (22)..(23)
<223> OTHER INFORMATION: n is 5-(N-benzylcarboxyamido)-2'-deoxyuridine
<220> FEATURE:
<221> NAME/KEY: misc_feature
<222> LOCATION: (25)..(26)
<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine
<220> FEATURE:
<221> NAME/KEY: misc_feature
<222> LOCATION: (34)..(36)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine

<400> SEQUENCE: 40
ancgcaggnn gnncggncgg anngnnggan nccnnnaagn ngg                         43

<210> SEQ ID NO 41
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (9)..(10)
<223> OTHER INFORMATION: n is 5-(N-benzylcarboxyamido)-2'-deoxyuridine
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (16)..(16)
<223> OTHER INFORMATION: n is 5-(N-benzylcarboxyamido)-2'-deoxyuridine
<220> FEATURE:
<221> NAME/KEY: misc_feature
<222> LOCATION: (22)..(23)
<223> OTHER INFORMATION: n is 5-(N-benzylcarboxyamido)-2'-deoxyuridine
<220> FEATURE:
<221> NAME/KEY: misc_feature
<222> LOCATION: (25)..(26)
<223> OTHER INFORMATION: n is 5-(N-benzylcarboxyamido)-2'-deoxyuridine
<220> FEATURE:
<221> NAME/KEY: misc_feature
<222> LOCATION: (31)..(31)
<223> OTHER INFORMATION: n is 5-(N-benzylcarboxyamido)-2'-deoxyuridine
<220> FEATURE:
<221> NAME/KEY: misc_feature
<222> LOCATION: (33)..(35)
<223> OTHER INFORMATION: n is 5-(N-benzylcarboxyamido)-2'-deoxyuridine
<220> FEATURE:
<221> NAME/KEY: misc_feature
<222> LOCATION: (38)..(38)
<223> OTHER INFORMATION: n is 5-(N-benzylcarboxyamido)-2'-deoxyuridine

<400> SEQUENCE: 41
ancgacggnn gnggannccgg anngnnggac ncnnnagng                             39
```

<210> SEQ ID NO 42
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (8)..(9)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(15)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (28)..(30)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(37)
<223> OTHER INFORMATION: n is 5-(N-benzylcarboxyamido)-2'-deoxyuridine

<400> SEQUENCE: 42
ancgaggnng ngggncggan ngnnggannn annaggng                                38

<210> SEQ ID NO 43
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (8)..(9)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (15)..(16)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine

```
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (31)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(37)
<223> OTHER INFORMATION: n is 5-(N-benzylcarboxyamido)-2'-deoxyuridine
<220> FEATURE:
<221> NAME/KEY: misc_feature
<222> LOCATION: (40)..(40)
<223> OTHER INFORMATION: n is 5-(N-benzylcarboxyamido)-2'-deoxyuridine

<400> SEQUENCE: 43
ancgaggnng ngggnnggan ngnnggannc nnnaacnggn                              40

<210> SEQ ID NO 44
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (4)..(4)
<223> OTHER INFORMATION: n is 5-(N-benzylcarboxyamido)-2'-deoxyuridine
<220> FEATURE:
<221> NAME/KEY: misc_feature
<222> LOCATION: (11)..(11)
<223> OTHER INFORMATION: n is 5-(N-benzylcarboxyamido)-2'-deoxyuridine
<220> FEATURE:
<221> NAME/KEY: misc_feature
<222> LOCATION: (13)..(13)
<223> OTHER INFORMATION: n is 5-(N-benzylcarboxyamido)-2'-deoxyuridine
<220> FEATURE:
<221> NAME/KEY: misc_feature
<222> LOCATION: (16)..(16)
<223> OTHER INFORMATION: n is 5-(N-benzylcarboxyamido)-2'-deoxyuridine
<220> FEATURE:
<221> NAME/KEY: misc_feature
<222> LOCATION: (21)..(22)
<223> OTHER INFORMATION: n is 5-(N-benzylcarboxyamido)-2'-deoxyuridine
<220> FEATURE:
<221> NAME/KEY: misc_feature
<222> LOCATION: (24)..(25)
<223> OTHER INFORMATION: n is 5-(N-benzylcarboxyamido)-2'-deoxyuridine
<220> FEATURE:
<221> NAME/KEY: misc_feature
<222> LOCATION: (29)..(30)
<223> OTHER INFORMATION: n is 5-(N-benzylcarboxyamido)-2'-deoxyuridine
<220> FEATURE:
<221> NAME/KEY: misc_feature
<222> LOCATION: (32)..(33)
<223> OTHER INFORMATION: n is 5-(N-benzylcarboxyamido)-2'-deoxyuridine
<220> FEATURE:
<221> NAME/KEY: misc_feature
<222> LOCATION: (37)..(37)
<223> OTHER INFORMATION: n is 5-(N-benzylcarboxyamido)-2'-deoxyuridine

<400> SEQUENCE: 44
angncgaggc ngnggncgga nngnnggann cnnaagng                                38

<210> SEQ ID NO 45
<211> LENGTH: 36
<212> TYPE: DNA
<213> ORGANISM: Artificial Sequence
<220> FEATURE:
```

```
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (9)..(9)
<223> OTHER INFORMATION: n is 5-(N-benzylcarboxyamido)-2'-deoxyuridine
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (17)..(18)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (25)..(26)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (31)..(32)
<223> OTHER INFORMATION: n is 5-(N-benzylcarboxyamido)-2'-deoxyuridine
<220> FEATURE:
<221> NAME/KEY: misc_feature
<222> LOCATION: (36)..(36)
<223> OTHER INFORMATION: n is 5-(N-benzylcarboxyamido)-2'-deoxyuridine

<400> SEQUENCE: 45
ancaggngng gncgganngn nggannncnna nnaggn                          36

<210> SEQ ID NO 46
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n is 5-(N-benzylcarboxyamido)-2'-deoxyuridine
<220> FEATURE:
<221> NAME/KEY: misc_feature
<222> LOCATION: (8)..(8)
<223> OTHER INFORMATION: n is 5-(N-benzylcarboxyamido)-2'-deoxyuridine
<220> FEATURE:
<221> NAME/KEY: misc_feature
<222> LOCATION: (12)..(12)
<223> OTHER INFORMATION: n is 5-(N-benzylcarboxyamido)-2'-deoxyuridine
<220> FEATURE:
<221> NAME/KEY: misc_feature
<222> LOCATION: (14)..(15)
<223> OTHER INFORMATION: n is 5-(N-benzylcarboxyamido)-2'-deoxyuridine
<220> FEATURE:
<221> NAME/KEY: misc_feature
<222> LOCATION: (18)..(18)
<223> OTHER INFORMATION: n is 5-(N-benzylcarboxyamido)-2'-deoxyuridine
<220> FEATURE:
<221> NAME/KEY: misc_feature
<222> LOCATION: (23)..(25)
<223> OTHER INFORMATION: n is 5-(N-benzylcarboxyamido)-2'-deoxyuridine
<220> FEATURE:
<221> NAME/KEY: misc_feature
```

```
<222> LOCATION: (27)..(27)
<223> OTHER INFORMATION: n is 5-(N-benzylcarboxyamido)-2'-deoxyuridine
<220> FEATURE:
<221> NAME/KEY: misc_feature
<222> LOCATION: (31)..(32)
<223> OTHER INFORMATION: n is 5-(N-benzylcarboxyamido)-2'-deoxyuridine
<220> FEATURE:
<221> NAME/KEY: misc_feature
<222> LOCATION: (34)..(35)
<223> OTHER INFORMATION: n is 5-(N-benzylcarboxyamido)-2'-deoxyuridine
<220> FEATURE:
<221> NAME/KEY: misc_feature
<222> LOCATION: (40)..(41)
<223> OTHER INFORMATION: n is 5-(N-benzylcarboxyamido)-2'-deoxyuridine

<400> SEQUENCE: 46
cgancagnag gnannggncg gannngngga nncnnaaagn ngg                             43

<210> SEQ ID NO 47
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is 5-(N-benzylcarboxyamido)-2'-deoxyuridine
<220> FEATURE:
<221> NAME/KEY: misc_feature
<222> LOCATION: (12)..(13)
<223> OTHER INFORMATION: n is 5-(N-benzylcarboxyamido)-2'-deoxyuridine
<220> FEATURE:
<221> NAME/KEY: misc_feature
<222> LOCATION: (15)..(16)
<223> OTHER INFORMATION: n is 5-(N-benzylcarboxyamido)-2'-deoxyuridine
<220> FEATURE:
<221> NAME/KEY: misc_feature
<222> LOCATION: (20)..(21)
<223> OTHER INFORMATION: n is 5-(N-benzylcarboxyamido)-2'-deoxyuridine
<220> FEATURE:
<221> NAME/KEY: misc_feature
<222> LOCATION: (23)..(25)
<223> OTHER INFORMATION: n is 5-(N-benzylcarboxyamido)-2'-deoxyuridine
<220> FEATURE:
<221> NAME/KEY: misc_feature
<222> LOCATION: (29)..(30)
<223> OTHER INFORMATION: n is 5-(N-benzylcarboxyamido)-2'-deoxyuridine
<220> FEATURE:
<221> NAME/KEY: misc_feature
<222> LOCATION: (34)..(34)
<223> OTHER INFORMATION: n is 5-(N-benzylcarboxyamido)-2'-deoxyuridine

<400> SEQUENCE: 47
nacagcgggc anngnnggan ncnnnaagnn acgnaaagc                                  39

<210> SEQ ID NO 48
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is 5-(N-benzylcarboxyamido)-2'-deoxyuridine
<220> FEATURE:
<221> NAME/KEY: misc_feature
<222> LOCATION: (5)..(5)
<223> OTHER INFORMATION: n is 5-(N-benzylcarboxyamido)-2'-deoxyuridine
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
```

```
<221> NAME/KEY: misc_feature
<222> LOCATION: (14)..(15)
<223> OTHER INFORMATION: n is 5-(N-benzylcarboxyamido)-2'-deoxyuridine
<220> FEATURE:
<221> NAME/KEY: misc_feature
<222> LOCATION: (17)..(18)
<223> OTHER INFORMATION: n is 5-(N-benzylcarboxyamido)-2'-deoxyuridine
<220> FEATURE:
<221> NAME/KEY: misc_feature
<222> LOCATION: (22)..(23)
<223> OTHER INFORMATION: n is 5-(N-benzylcarboxyamido)-2'-deoxyuridine
<220> FEATURE:
<221> NAME/KEY: misc_feature
<222> LOCATION: (25)..(27)
<223> OTHER INFORMATION: n is 5-(N-benzylcarboxyamido)-2'-deoxyuridine
<220> FEATURE:
<221> NAME/KEY: misc_feature
<222> LOCATION: (31)..(32)
<223> OTHER INFORMATION: n is 5-(N-benzylcarboxyamido)-2'-deoxyuridine
<220> FEATURE:
<221> NAME/KEY: misc_feature
<222> LOCATION: (35)..(35)
<223> OTHER INFORMATION: n is 5-(N-benzylcarboxyamido)-2'-deoxyuridine

<400> SEQUENCE: 48
ngganangag gganngnngg anncnnnaag nngcncagaa                40

<210> SEQ ID NO 49
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is 5-(N-benzylcarboxyamido)-2'-deoxyuridine
<220> FEATURE:
<221> NAME/KEY: misc_feature
<222> LOCATION: (5)..(5)
<223> OTHER INFORMATION: n is 5-(N-benzylcarboxyamido)-2'-deoxyuridine
<220> FEATURE:
<221> NAME/KEY: misc_feature
<222> LOCATION: (7)..(7)
<223> OTHER INFORMATION: n is 5-(N-benzylcarboxyamido)-2'-deoxyuridine
<220> FEATURE:
<221> NAME/KEY: misc_feature
<222> LOCATION: (14)..(15)
<223> OTHER INFORMATION: n is 5-(N-benzylcarboxyamido)-2'-deoxyuridine
<220> FEATURE:
<221> NAME/KEY: misc_feature
<222> LOCATION: (17)..(18)
<223> OTHER INFORMATION: n is 5-(N-benzylcarboxyamido)-2'-deoxyuridine
<220> FEATURE:
<221> NAME/KEY: misc_feature
<222> LOCATION: (22)..(23)
<223> OTHER INFORMATION: n is 5-(N-benzylcarboxyamido)-2'-deoxyuridine
<220> FEATURE:
<221> NAME/KEY: misc_feature
<222> LOCATION: (26)..(27)
<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine
<220> FEATURE:
<221> NAME/KEY: misc_feature
<222> LOCATION: (34)..(34)
<223> OTHER INFORMATION: n is 5-(N-benzylcarboxyamido)-2'-deoxyuridine

<400> SEQUENCE: 49
ngganangag gcanngnngg anncennagn ngcncgaa                  38

<210> SEQ ID NO 50
<211> LENGTH: 40
```

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is 5-(N-benzylcarboxyamido)-2'-deoxyuridine
<220> FEATURE:
<221> NAME/KEY: misc_feature
<222> LOCATION: (6)..(6)
<223> OTHER INFORMATION: n is 5-(N-benzylcarboxyamido)-2'-deoxyuridine
<220> FEATURE:
<221> NAME/KEY: misc_feature
<222> LOCATION: (8)..(8)
<223> OTHER INFORMATION: n is 5-(N-benzylcarboxyamido)-2'-deoxyuridine
<220> FEATURE:
<221> NAME/KEY: misc_feature
<222> LOCATION: (14)..(16)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (23)..(24)
<223> OTHER INFORMATION: n is 5-(N-benzylcarboxyamido)-2'-deoxyuridine
<220> FEATURE:
<221> NAME/KEY: misc_feature
<222> LOCATION: (26)..(27)
<223> OTHER INFORMATION: n is 5-(N-benzylcarboxyamido)-2'-deoxyuridine
<220> FEATURE:
<221> NAME/KEY: misc_feature
<222> LOCATION: (31)..(32)
<223> OTHER INFORMATION: n is 5-(N-benzylcarboxyamido)-2'-deoxyuridine
<220> FEATURE:
<221> NAME/KEY: misc_feature
<222> LOCATION: (35)..(35)
<223> OTHER INFORMATION: n is 5-(N-benzylcarboxyamido)-2'-deoxyuridine

<400> SEQUENCE: 50
nggacnanga ggannngnng ganncnnaag nngcncagaa                           40

<210> SEQ ID NO 51
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n is 5-(N-benzylcarboxyamido)-2'-deoxyuridine
<220> FEATURE:
<221> NAME/KEY: misc_feature
<222> LOCATION: (4)..(5)
<223> OTHER INFORMATION: n is 5-(N-benzylcarboxyamido)-2'-deoxyuridine
<220> FEATURE:
<221> NAME/KEY: misc_feature
<222> LOCATION: (9)..(9)
<223> OTHER INFORMATION: n is 5-(N-benzylcarboxyamido)-2'-deoxyuridine
<220> FEATURE:
<221> NAME/KEY: misc_feature
<222> LOCATION: (13)..(14)
<223> OTHER INFORMATION: n is 5-(N-benzylcarboxyamido)-2'-deoxyuridine
<220> FEATURE:
<221> NAME/KEY: misc_feature
<222> LOCATION: (16)..(17)
<223> OTHER INFORMATION: n is 5-(N-benzylcarboxyamido)-2'-deoxyuridine
<220> FEATURE:
<221> NAME/KEY: misc_feature
<222> LOCATION: (21)..(22)
<223> OTHER INFORMATION: n is 5-(N-benzylcarboxyamido)-2'-deoxyuridine
<220> FEATURE:
<221> NAME/KEY: misc_feature
<222> LOCATION: (24)..(26)
```

<223> OTHER INFORMATION: n is 5-(N-benzylcarboxyamido)-2'-deoxyuridine
<220> FEATURE:
<221> NAME/KEY: misc_feature
<222> LOCATION: (30)..(31)
<223> OTHER INFORMATION: n is 5-(N-benzylcarboxyamido)-2'-deoxyuridine

<400> SEQUENCE: 51
cnanngagng canngnnaga nncnnnaagn ncggaaccag                                40

<210> SEQ ID NO 52
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is 5-(N-benzylcarboxyamido)-2'-deoxyuridine
<220> FEATURE:
<221> NAME/KEY: misc_feature
<222> LOCATION: (4)..(4)
<223> OTHER INFORMATION: n is 5-(N-benzylcarboxyamido)-2'-deoxyuridine
<220> FEATURE:
<221> NAME/KEY: misc_feature
<222> LOCATION: (6)..(6)
<223> OTHER INFORMATION: n is 5-(N-benzylcarboxyamido)-2'-deoxyuridine
<220> FEATURE:
<221> NAME/KEY: misc_feature
<222> LOCATION: (10)..(11)
<223> OTHER INFORMATION: n is 5-(N-benzylcarboxyamido)-2'-deoxyuridine
<220> FEATURE:
<221> NAME/KEY: misc_feature
<222> LOCATION: (13)..(14)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (21)..(23)
<223> OTHER INFORMATION: n is 5-(N-benzylcarboxyamido)-2'-deoxyuridine
<220> FEATURE:
<221> NAME/KEY: misc_feature
<222> LOCATION: (27)..(28)
<223> OTHER INFORMATION: n is 5-(N-benzylcarboxyamido)-2'-deoxyuridine
<220> FEATURE:
<221> NAME/KEY: misc_feature
<222> LOCATION: (39)..(40)
<223> OTHER INFORMATION: n is 5-(N-benzylcarboxyamido)-2'-deoxyuridine

<400> SEQUENCE: 52
nggngnggan ngnnagannc nnnaagnncg cgggcaccnn                                40

<210> SEQ ID NO 53
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n is 5-(N-benzylcarboxyamido)-2'-deoxyuridine
<220> FEATURE:
<221> NAME/KEY: misc_feature
<222> LOCATION: (10)..(11)
<223> OTHER INFORMATION: n is 5-(N-benzylcarboxyamido)-2'-deoxyuridine
<220> FEATURE:
<221> NAME/KEY: misc_feature
<222> LOCATION: (13)..(14)
<223> OTHER INFORMATION: n is 5-(N-benzylcarboxyamido)-2'-deoxyuridine
<220> FEATURE:
<221> NAME/KEY: misc_feature
<222> LOCATION: (18)..(19)
<223> OTHER INFORMATION: n is 5-(N-benzylcarboxyamido)-2'-deoxyuridine
<220> FEATURE:
<221> NAME/KEY: misc_feature
<222> LOCATION: (21)..(23)
<223> OTHER INFORMATION: n is 5-(N-benzylcarboxyamido)-2'-deoxyuridine
<220> FEATURE:
<221> NAME/KEY: misc_feature
<222> LOCATION: (28)..(29)
<223> OTHER INFORMATION: n is 5-(N-benzylcarboxyamido)-2'-deoxyuridine
<220> FEATURE:
<221> NAME/KEY: misc_feature
<222> LOCATION: (32)..(32)
<223> OTHER INFORMATION: n is 5-(N-benzylcarboxyamido)-2'-deoxyuridine
<220> FEATURE:
<221> NAME/KEY: misc_feature
<222> LOCATION: (35)..(36)
<223> OTHER INFORMATION: n is 5-(N-benzylcarboxyamido)-2'-deoxyuridine
<220> FEATURE:
<221> NAME/KEY: misc_feature
<222> LOCATION: (39)..(39)
<223> OTHER INFORMATION: n is 5-(N-benzylcarboxyamido)-2'-deoxyuridine

<400> SEQUENCE: 53
ggacangaan ngnnagannc nnnaaagnna gnggnnacng a                41

<210> SEQ ID NO 54
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n is 5-(N-benzylcarboxyamido)-2'-deoxyuridine
<220> FEATURE:
<221> NAME/KEY: misc_feature
<222> LOCATION: (9)..(10)
<223> OTHER INFORMATION: n is 5-(N-benzylcarboxyamido)-2'-deoxyuridine
<220> FEATURE:
<221> NAME/KEY: misc_feature
<222> LOCATION: (12)..(13)
<223> OTHER INFORMATION: n is 5-(N-benzylcarboxyamido)-2'-deoxyuridine
<220> FEATURE:
<221> NAME/KEY: misc_feature
<222> LOCATION: (17)..(18)
<223> OTHER INFORMATION: n is 5-(N-benzylcarboxyamido)-2'-deoxyuridine
<220> FEATURE:
<221> NAME/KEY: misc_feature
<222> LOCATION: (20)..(22)
<223> OTHER INFORMATION: n is 5-(N-benzylcarboxyamido)-2'-deoxyuridine
<220> FEATURE:
<221> NAME/KEY: misc_feature
<222> LOCATION: (26)..(27)
<223> OTHER INFORMATION: n is 5-(N-benzylcarboxyamido)-2'-deoxyuridine
<220> FEATURE:
<221> NAME/KEY: misc_feature
<222> LOCATION: (39)..(39)
<223> OTHER INFORMATION: n is 5-(N-benzylcarboxyamido)-2'-deoxyuridine

<400> SEQUENCE: 54
ggggngaann gnnaganncn nnaagnncgg ggcgcaccn                  39

<210> SEQ ID NO 55
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is g, c, or a
<220> FEATURE:

```
<221> NAME/KEY: misc_feature
<222> LOCATION: (4)..(5)
<223> OTHER INFORMATION: n is independently, a 5-position modified
      2'-deoxyuridine
<220> FEATURE:
<221> NAME/KEY: misc_feature
<222> LOCATION: (7)..(8)
<223> OTHER INFORMATION: n is independently, a 5-position modified
      2'-deoxyuridine
<220> FEATURE:
<221> NAME/KEY: misc_feature
<222> LOCATION: (9)..(9)
<223> OTHER INFORMATION: n is g or a
<220> FEATURE:
<221> NAME/KEY: misc_feature
<222> LOCATION: (12)..(13)
<223> OTHER INFORMATION: n is independently, a 5-position modified
      2'-deoxyuridine
<220> FEATURE:
<221> NAME/KEY: misc_feature
<222> LOCATION: (15)..(16)
<223> OTHER INFORMATION: n is independently, a 5-position modified
      2'-deoxyuridine

<400> SEQUENCE: 55
nganngnnng anncnn                                                       16
```

APTAMERS AND DIAGNOSTIC METHODS FOR DETECTING THE EGF RECEPTOR

RELATED APPLICATIONS

This application is a 35 U.S.C. §371 national phase application of International Application Serial No. PCT/US2012/072101, filed Dec. 28, 2012 (WO 2013/102101). International Application Serial No. PCT/US2012/072101 claims priority to U.S. Provisional Application Ser. No. 61/582,111, filed Dec. 30, 2011; U.S. Provisional Application Ser. No. 61/649,168, filed May 18, 2012 and U.S. Provisional Application Ser. No. 61/655,404, filed Jun. 4, 2012. Each of these applications is incorporated by reference in its entirety.

FIELD OF THE INVENTION

The invention relates to the field of cancer diagnosis and treatment. Specifically, the invention provides compositions and methods for binding the EGF receptor when it is not bound to a therapeutic molecule, as well as methods of determining cancer resistance to therapeutic molecules.

Incorporated by reference herein in its entirety is the Sequence Listing entitled "sequence Listing.txt", created Jan. 23, 2013, size of 59 kilobytes.

BACKGROUND OF THE INVENTION

The following description of the background of the invention is provided simply as an aid in understanding the invention and is not admitted to describe or constitute prior art to the invention.

The Epidermal Growth Factor receptor (EGFR; also known as HER1 or ErbB-1) is a transmembrane tyrosine kinase receptor expressed on epithelial cells that is strongly linked to several cancers, including but not limited to head and neck squamous cell carcinoma (HNSCC), non-small cell lung cancer (NSCLC), colorectal cancer (CRC), breast cancer, pancreatic cancer, and brain cancer. The EGFR is shed in both healthy patients and cancer patients and is detectable in their serum. Serum levels of EGFR in cancer patients are known to vary from EGFR levels measured in healthy controls.

The therapeutic antibodies cetuximab (Erbitux™) and panitumumab (Vectibix™) were developed for use as targeted therapies that recognize and inhibit the extracellular domain of EGFR. Cetuximab is approved by the FDA for use as an intravenous treatment for head and neck cancer and colorectal carcinoma, while panitumumab is approved by the FDA for use as a treatment for colorectal cancer.

Some patients have cancer that is resistant or becomes resistant to treatment with cetuximab or panitumumab (see Carney, Expert Rev Mol Diagn. 2007 May; 7(3):309-19; Wheeler, et al., Oncogene. 2008 Jun. 26; 27(28): 3944-3956; Bardelli, et al., J Clin Oncol. 2010 Mar. 1; 28(7):1254-61). Therefore it is desirable for doctors to monitor ongoing therapy to determine whether cancer cell resistance to the therapeutic antibodies is increasing, and modify the treatment accordingly. It is also desirable for doctors to determine whether all of the soluble EGFR is bound to the therapeutic antibodies.

SUMMARY OF THE INVENTION

The claimed invention provides aptamers that bind free EGFR in a sample, as well as methods of determining the amount of free EGFR in a sample and methods of optimizing therapeutic efficacy for treatment of cancer.

In one aspect, the claimed invention provides aptamers including the structure defined by SEQ ID NO: 1. In some embodiments, the aptamers include a 3' cap. In some embodiments, the 3' cap is an inverted deoxythymidine. In some embodiments the aptamers include a spacer and at least one moiety selected from the group consisting of a binding pair member and a detectable label, wherein the spacer is attached to the 5'-end of the aptamer and the moiety is attached to the 5' end of the spacer. In some embodiments the spacer is hexaethylene glycol. In some embodiments, the binding pair member is biotin. In some embodiments the detectable label is a fluorophore. In some embodiments the aptamers include the structure defined by SEQ ID NO: 4. In some embodiments the aptamers include the structure defined by SEQ ID NO: 5. In some embodiments the aptamers include the structure defined by SEQ ID NO: 6. In some embodiments the aptamers include the structure defined by SEQ ID NO: 7. In some embodiments the aptamers include the structure defined by SEQ ID NO: 8. In some embodiments the aptamers include the structure defined by SEQ ID NOS: 1 to 55.

In another aspect, the claimed invention provides methods for determining the amount of free Epidermal Growth Factor receptor (EGFR) in a sample including: (a) contacting a sample with an aptamer that specifically binds to free EGFR under conditions that allow binding of the aptamer to the free EGFR in the sample to form an aptamer-EGFR complex; (b) determining the amount of the free EGFR bound by the aptamer; and (c) relating the amount of free EGFR bound by the aptamer to the amount of free EGFR in the sample. In some embodiments the aptamer includes the structure defined by SEQ ID NO: 1. In some embodiments the aptamer includes the structure defined by SEQ ID NO: 4. In some embodiments the aptamers include the structure defined by SEQ ID NO: 5. In some embodiments the aptamers include the structure defined by SEQ ID NO: 6. In some embodiments the aptamers include the structure defined by SEQ ID NO: 7. In some embodiments the aptamers include the structure defined by SEQ ID NO: 8. In some embodiments the aptamers include the structure defined by SEQ ID NOS: 1 to 55. In some embodiments the aptamer includes a first binding pair member and is immobilized on a first solid support via a second binding pair member that specifically binds to the first binding pair member. In some embodiments, the sample is contacted with the aptamer prior to immobilization on the first solid support. In some embodiments the sample is contacted with the aptamer after immobilization on the first solid support. In some embodiments, the amount of free EGFR is determined by determining the amount of EGFR immobilized on the first solid support. In some embodiments the amount of EGFR is determined using an antibody that specifically binds to the immobilized EGFR.

In some embodiments the methods further include: (i) attaching a third binding pair member to the EGFR; (ii) releasing the aptamer-EGFR complex from the solid support; (iii) immobilizing the aptamer-EGFR complex on a second solid support via a fourth binding pair member that specifically binds to the third binding pair member; and (iv) determining the amount of EGFR immobilized to the second solid support. In some embodiments, the amount of EGFR immobilized on the second solid support is determined using an antibody that specifically binds to EGFR. In some embodiments, the methods further include labeling the EGFR with a detectable label either before or after immobilization on the second solid support. In some embodiments, the aptamer further includes a detectable label. In some embodiments the amount of EGFR immobilized on the solid support is determined using flow cytometry. In some embodiments the amount of EGFR immobilized on the second solid support is determined by releasing the aptamer from the aptamer-EGFR complex and determining the amount of the released aptamer. In some embodiments, the amount of the released aptamer is determined by amplification of the aptamer.

In yet another aspect, the claimed invention provides methods of optimizing therapeutic efficacy for treatment of cancer comprising: determining the amount of free EGFR and total EGFR in a sample from a patient being treated with a therapeutic molecule that binds the extracellular domain of the Epithelial Growth Factor receptor (EGFR); identifying a need to increase the dose of the therapeutic molecule administered to the patient when the proportion of free EGFR to total EGFR in the sample is greater than a predetermined threshold, and identifying that the dose of the therapeutic molecule does not need to be increased when the proportion of free EGFR to total EGFR in the sample is less than a predetermined threshold, wherein the threshold is about 10%. In some embodiments, the threshold is about 1%; is about 2%; is about 3%; is about 4%; is about 5%; is about 10%; is about 15%; is about 20%; is about 25%; is about 30%; is about 35%; is about 40%; is about 45%; is about 50%.

In some embodiments, the patient has an epithelial carcinoma. In some embodiments the epithelial carcinoma is selected from the group consisting of a squamous cell carcinoma, an adenocarcinoma, and a transitional cell carcinoma. In some embodiments, the methods further include relating the amount of free EGFR to the amount of bound EGFR. In some embodiments the methods further include predicting poor carcinoma response to continued administration of the therapeutic molecule if the amount of free EGFR is too high.

As used herein, unless otherwise stated, the singular forms "a," "an," and "the" include plural reference. Thus, for example, a reference to "a protein" includes a plurality of protein molecules.

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

As used herein, the term "aptamer" refers to an oligonucleotide that can conform in three-dimensions to bind another molecule with high affinity and specificity.

As used herein, the term "cap" refers to a moiety attached to the 3' or 5' end of an aptamer or other nucleic acid that changes the stability of the nucleic acid, prevents polymerase elongation of the nucleic acid, or increases the efficiency of nucleic acid dimer formation. The term "capping" refers to the process of adding a cap.

As used herein, "consensus sequence", when used in reference to a series of related nucleic acids, refers to a nucleotide sequence that reflects the most common choice of base at each position in the sequence where the series of related nucleic acids has been subjected to intensive mathematical and/or sequence analysis.

As used herein, the term "free EGFR" refers to Epidermal Growth Factor receptor (EGFR) or a portion thereof that is not bound, either covalently or non-covalently, to a therapeutic molecule (e.g., an antagonist). Therapeutic molecules include any exogenous molecule that binds EGFR and modifies its biological activity including, for example, a therapeutic antibody (e.g., cetuximab and panitumumab), a small molecule, or an aptamer. Free EGFR may be bound to other endogenous and/or non-therapeutic molecules.

As used herein, the term "bound EGFR" refers to Epidermal Growth Factor receptor (EGFR) that is bound, either covalently or non-covalently, to an exogenously-administered therapeutic molecule. Therapeutic molecules may include any molecule that binds EGFR and modifies its biological activity including, for example, a therapeutic antibody, a small molecule, or an aptamer.

As used herein the term "binding agent" means a molecule that binds to a cognate ligand with high affinity and high specificity. A binding agent is typically used to identify the presence of its cognate ligand and can be detectably labeled to allow identification. An "EGFR binding agent" means a molecule that binds to EGFR with high affinity and high specificity. Examples of EGFR binding agents include antibodies, aptamers, and ligands of EGFR. EGFR binding agents include Epidermal Growth Factor (EGF), Transforming Growth Factor α (TGFα), Heparin-Binding EGF-like Growth Factor (HB-EGF), amphiregulin, betacellulin, epigen, and epiregulin.

As used herein, the term "binding pair" refers to a pair of molecules that bind to each other with high affinity and specificity. A "binding pair member" refers to one molecule of a binding pair. For example, streptavidin and biotin are binding pair members that non-covalently bind with each other. Other exemplary binding pairs include protein A and the Fc domain of IgG, Fab region of an antibody and its antigen, and a single oligonucleotide strand and its complement.

As used herein, the term "detectable label" refers to a molecule or a compound or a group of molecules or a group of compounds associated with a nucleic acid or a polypeptide and is used to identify the nucleic acid or the polypeptide. Signals from the detectable label may be detected by various means and will depend on the nature of the detectable label. Detectable labels may be isotopes, fluorescent moieties, colored substances, enzymes, enzyme substrates, and the like. Examples of means to detect detectable label include but are not limited to spectroscopic, photochemical, biochemical, immunochemical, electromagnetic, radiochemical, or chemical means, such as fluorescence, chemifluorescence, or chemiluminescence, or any other appropriate means.

As used herein, the term "amplification" means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

As used herein, the term "specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

As used herein, the term "sample" means any tissue or body fluid that can be isolated from the body of an individual. For example, a sample may include a tissue biopsy, blood, plasma, serum, bile, saliva, urine, tears, perspiration, and the like.

The summary of the invention described above is non-limiting and other features and advantages of the invention will be apparent from the following detailed description of the invention, and from the claims.

BRIEF DESCRIPTION OF THE DRAWINGS

FIGS. 4A and 4B show tables providing sequence data and $K_d$ data for several aptamers (SEQ ID NOs: 9-33) to EGFR (as known as ERBB1).

FIG. 9 illustrates quantitation of EGFR in serum pre-incubated with panitumumab or cetuximab. Preincubation had little effect on ELISA quantitation but decreased SOMAmer quantitation in a dose-dependent manner.

FIG. 10 illustrates 21 unique aptamer sequences (SEQ ID NOs: 34-54) identified from the 1425 sequences isolated from the SELEX process as described in Example 1 when multiple copies are taken into account. The sequences are shown 5' to 3', wherein all T's are 5-(N-benzylcarboxyamido)-2'-deoxyuracilyl (BndU).

FIG. 11 illustrates an aptamer consensus frequency table for aptamer consensus sequence SEQ ID NO: 55. The table summarizes the consensus as a frequency matrix in (1) unique counts and (20 total copy counts).

DETAILED DESCRIPTION OF THE INVENTION

Figure 1:
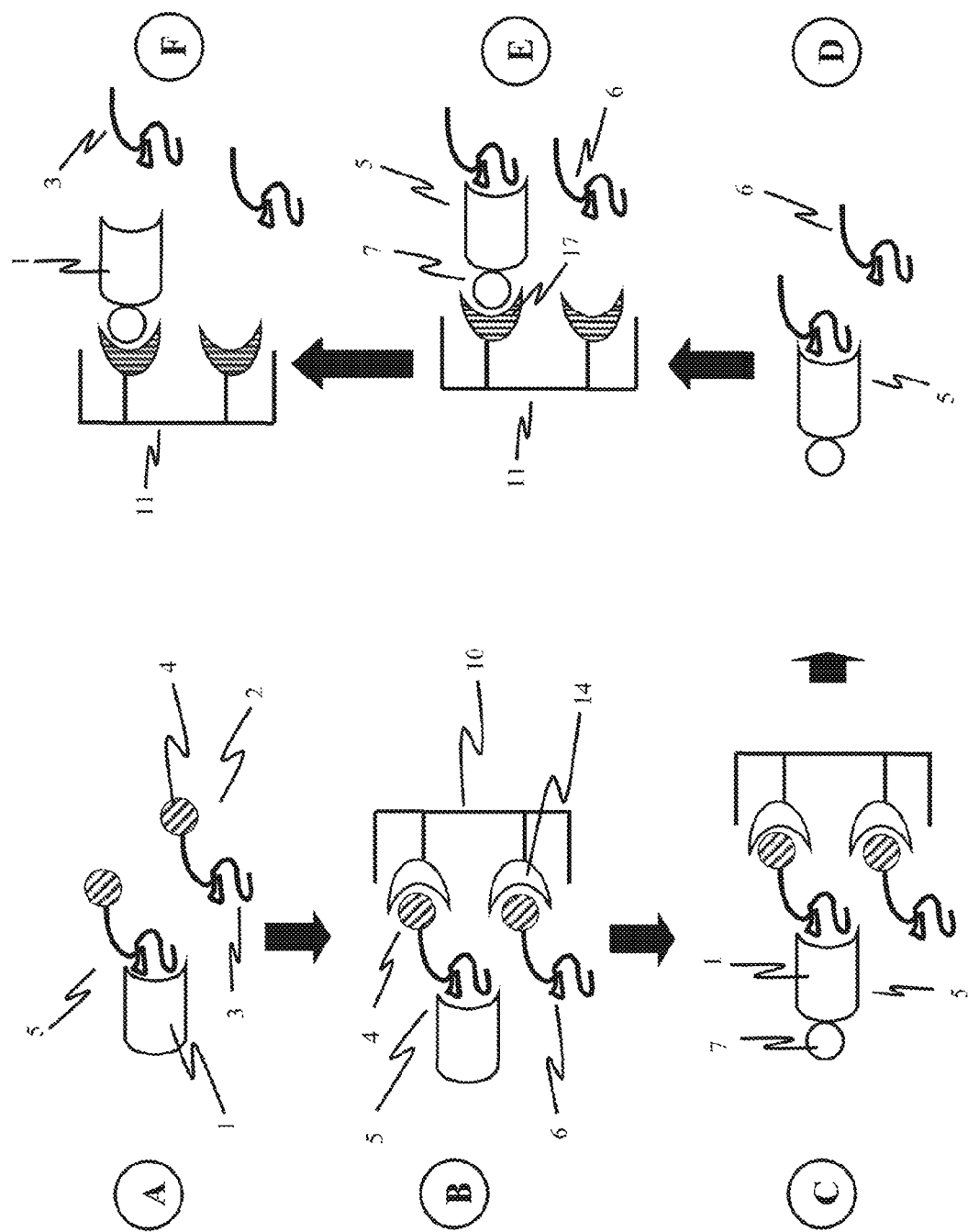
FIG. 1 shows a schematic diagram of a detection method using an aptamer to bind and detect a molecule.

Methods using aptamers to detect EGFR have been described in the art. For example, Esposito, et al. (PLoS One. 2011; 6(9):e24071) described isolation of an aptamer that binds the extracellular domain of EGFR and inhibits tumor growth in a mouse model of NSCLC. Li, et al. (PLoS One. 2011; 6(6):e20299) also describe isolation of an aptamer that binds EGFR in a tumor cell line.

The present invention relates generally to an aptamer that binds with high affinity and specificity to free EGFR in patient samples. Specifically, embodiments of the invention include aptamer compositions, as well as methods of detecting free EGFR in a sample, and methods of determining whether a cancer is becoming resistant to treatment with a therapeutic molecule.

Aptamers

Aptamers are oligonucleotides that can form a three-dimensional structure that binds another molecule with high affinity and specificity, similar to that of an antibody. Because of their ability to bind a variety of ligands and the ease and range of options for functionalization of nucleic acids, aptamers have been used in place of antibodies in a variety of therapeutic and diagnostic applications. For example, pegaptinib is an FDA approved nucleic acid aptamer developed by Macugen, Inc. that inhibits the activity of vascular endothelial growth factor to treat neovascularization in age-related macular degeneration. Nucleic acid aptamers have been used as capture moieties, as well as detection moieties in ELISA-like assays for detecting tularemia antigen (Vivekananda, et al., Lab Invest. 2006 June; 86(6):610-8). Aptamers have also been used in proteomics assays, affinity chromatography, liquid chromatography, and biosensors (for example, see Iliuk, et al., Anal Chem. 2011 Jun. 15; 83(12):4440-52; Lee, et al., Adv Drug Deliv Rev. 2010 Apr. 30; 62(6):592-605; Mairal, et al., Anal Bioanal Chem. 2008 February; 390(4): 989-1007; Ravelet, et al., J Chromatogr A. 2006 Jun. 2; 1117 (1):1-10).

Aptamer Design

Nucleic acid aptamers are created using an in vitro process known as systematic evolution of ligands by exponential enrichment (SELEX). Briefly, the selection process uses a combinatorial oligonucleotide library in which each oligonucleotide has central region of variable nucleic acids flanked by two regions of fixed sequence. The variable region of each candidate in the library can be totally or partially randomized. The oligonucleotide library is exposed to a target, such as a protein, under conditions that allow favorable binding between oligonucleotide candidates and the target. Following binding, a selective partitioning step is utilized, in which non-binding or poorly binding oligonucleotides are removed from the mixture, and the oligonucleotide candidates that bound to the target are then removed from the target molecule. These selected oligonucleotides are then enriched using PCR amplification with primers to the fixed regions of the oligonucleotide candidates. This process of binding, selective partitioning, and amplifying the selected candidate oligonucleotides is repeated for several rounds. Finally, the selected sequences are cloned and sequenced.

The basic SELEX process has been modified to achieve a number of specific objectives. For example, U.S. Pat. App. No. 2009/0098549 entitled "SELEX AND PHOTOSELEX" describes methods using the SELEX process to generate photoreactive nucleic acid ligands that are capable of both binding and covalently crosslinking to target molecules. U.S. Pat. No. 5,707,796, entitled "Method for Selecting Nucleic Acids on the Basis of Structure" describes the use of the SELEX process in conjunction with gel electrophoresis to select nucleic acid molecules with specific structural characteristics, such as bent DNA. U.S. Pat. No. 5,580,737, entitled "High-Affinity Nucleic Acid Ligands That Discriminate Between Theophylline and Caffeine" describes a method for identifying highly specific nucleic acid ligands able to discriminate between closely related molecules, termed Counter-SELEX. U.S. Pat. No. 5,567,588, entitled "Systematic Evolution of Ligands by Exponential Enrichment: Solution SELEX" describes a SELEX-based method which achieves highly efficient partitioning between oligonucleotides having high and low affinity for a target molecule. U.S. Pat. No. 5,496,938, entitled "Nucleic Acid Ligands to HIV RT and HIV-I Rev" describes methods for obtaining improved nucleic acid ligands after SELEX has been performed. U.S. Pat. No. 5,705,337, entitled "Systematic Evolution of Ligands by Exponential Enrichment ChemiSELEX" describes methods for covalently linking a nucleic acid ligand to its target.

Nucleotides used in the oligonucleotide library can be modified in any number of ways, including modifications of the ribose and/or phosphate and/or base positions. Certain modifications are described in U.S. Pat. No. 5,660,985 entitled "High Affinity Nucleic Acid Ligands Containing Modified Nucleotides", U.S. Pat. No. 5,428,149 entitled "Method for Palladium Catalyzed Carbon-Carbon Coupling and Products", U.S. Pat. No. 5,580,972 entitled "Purine Nucleoside Modifications by Palladium Catalyzed Methods", U.S. Pat. No. 5,719,273 entitled "Nucleoside modifications by palladium catalyzed methods" all of which are incorporated by reference herein in their entirety. In one embodiment, modifications are those wherein another chemical group is attached to the 5-position of a pyrimidine or the 2' position of a sugar. There is no limitation on the type of other chemical group that can be incorporated on the individual nucleotides. In some embodiments, the resulting modified nucleotide is amplifiable or can be modified subsequent to the amplification steps (see, e.g., U.S. Pat. No. 6,300,074 entitled "Systematic evolution of ligands by exponential enrichment: ChemiSELEX").

Aptamer-Based Assays

Assays that use an aptamer to indirectly detect its cognate ligand are described, for example, in U.S. Pat. No. 7,855,054. In these types of assays, an aptamer construct is used to capture a ligand on a solid support, and contacts a sample that may contain the ligand of the aptamer. The aptamer-ligand complex is partitioned from aptamers that are not bound to the ligand, and the aptamer portion of the aptamer-ligand complex is then separated from the ligand. The amount of ligand in the sample is then measured indirectly by detecting and quantifying the amount of aptamer that was bound to the sample ligand. Alternatively, the ligand captured from the sample is measured directly using an antibody or another aptamer that binds to the ligand.

Dual Capture Assay for EGFR

One embodiment of an aptamer-based assay is illustrated in FIG. 1. Referring to step A of FIG. 1, a test sample that may contain a target molecule of interest (hereinafter called a ligand (1)), such as EGFR, is incubated with an aptamer construct (2) that includes an aptamer (3) and a first binding pair member (4) (e.g. biotin), that has specific affinity for the ligand. If the sample contains the ligand, the aptamer binds to the ligand, forming an aptamer-ligand complex (5). The aptamer does not bind non-target molecules in the sample with the same high affinity and specificity as the ligand.

Referring to step B of FIG. 1, the incubated mixture is contacted with a first solid support (10) on which is immobilized a second binding pair member (14) that specifically binds to the first binding pair member (4) (e.g. streptavidin or an antibody that binds biotin). The aptamer-ligand complex (5) and uncomplexed aptamer (6) are captured on the solid support (10) via the second binding pair member (14). Alternatively, the aptamer complex may be captured on the solid support (10) via the binding pair members prior to exposure to the ligand-containing sample. Supporting either event, the solid support is washed to remove unbound sample and reagent components.

Referring to step C of FIG. 1, the captured ligand (1) of the aptamer-ligand complex (5) is labeled with a third binding pair member (7) (e.g. biotin).

Referring to step D of FIG. 1, the aptamer-ligand complex (5) and uncomplexed aptamer (6) are released from the first solid support using a method appropriate to the particular binding pair member being employed. For example, biotin may be attached to the aptamer using a photocleavable linkage. When the complex is exposed to ultraviolet (UV) light, the linkage is cleaved, freeing the aptamer-ligand complex (5) and uncomplexed aptamer (6) from the first solid support. If the first binding pair member is not removed from the aptamer during release from the solid support, the first binding pair member may be optionally removed from the aptamer after release in order that the same binding pair member species may be used during later processing without interference.

Optionally, a kinetic challenge can be performed to increase the assay specificity and decrease the background signal. The application of a kinetic challenge to an assay employing aptamers eliminates the need to enhance specificity by introducing a second capture reagent, such as an antibody used in a sandwich ELISA assay. If a kinetic challenge is introduced, non-specific complexes between the aptamer and any non-target molecules are unlikely to re-form following their dissociation. Since non-specific complexes generally dissociate more rapidly than an aptamer affinity complex, a kinetic challenge reduces the likelihood that an aptamer will be involved in a non-specific complex with a non-target molecule.

Kinetic challenge molecules include any molecule that can prevent non-specific binding of a non-target molecule to an aptamer. Kinetic challenge molecules include oligonucleotides, polyanions (e.g., heparin, herring sperm DNA, single-stranded salmon sperm DNA, and polydextrans, such as dextran sulfate), abasic phosphodiester polymers, dNTPs, and pyrophosphate. A kinetic challenge molecule can also be any molecule that can form a non-specific complex with a free aptamer, for example to prevent that aptamer from rebinding non-specifically to a non-target molecule. Such kinetic challenge molecules include polycations (e.g., spermine, spermidine, polylysine, and polyarginine) and amino acids (e.g., arginine and lysine). When a competitor is used as the kinetic challenge a fairly high concentration is utilized relative to the anticipated concentration of total protein or total aptamer present in the sample. In one embodiment, about 10 mM dextran sulfate is used as the competitor in a kinetic challenge.

Referring to step E of FIG. 1, following release of the aptamer-ligand complex (5) and the uncomplexed aptamer (6) from the first solid support and optional kinetic challenge, a fourth binding pair member (17) (e.g. streptavidin or an antibody against biotin) bound to a second solid support (11) is used to immobilize the released aptamer-ligand complex (5). The second solid support is then washed to remove the uncomplexed aptamers (6) and other molecules not attached to the second solid support.

Referring to step F of FIG. 1, following capture of aptamer-ligand complex on the second solid support (11), the aptamer (3) is released from the complex. Aptamer release may be affected by contacting the immobilized complex with a solution (e.g. high pH solution) that permits the aptamer (3) to dissociate from the ligand (1).

Following dissociation of the aptamer (3) from the ligand (1), the amount of ligand (3) may be detected or quantitated either directly or indirectly. Ligand (1) may be measured directly by contacting the ligand (1) with a detectably labeled binding agent (e.g. an aptamer or antibody). Alternatively, or in addition, ligand (1) may be measured indirectly by detecting the presence and/or amount of the released aptamer (3). Aptamers which include an oligonucleotide portion may be detected and/or quantitated using any suitable nucleic acid detection technique, such as, for example, probe hybridization (e.g. using probes immobilized on solid substrates such as beads or a microarray, or using detectably-labeled probes), quantitative PCR (qPCR), mass spectroscopy (MS), a combination probe-bead PCR amplification (such as a Luminex™ assay), the Invader assay, and the like. Depending on which technique is employed, the aptamer may be designed or modified to include a detectable label if direct detection of the aptamer is desired. Aptamer labeling may be accomplished during synthesis (either enzymatically or chemically) or at any time during the assay (i.e., at any time prior to detection).

Single-Support Sandwich Detection of EGFR

Aptamers may substitute for antibodies or other ligands that bind with specificity and are used to detect other molecules. Thus, an analyte in a sample, e.g. free EGFR, may be detected using an aptamer specific for the analyte in a single-support sandwich-style assay similar to an enzyme-linked immunosorbent assay (ELISA). The aptamer can be used to either capture the analyte or to detect the analyte.

An aptamer (2) specific for a ligand (1), such as EGFR, can be used to capture the ligand on a solid support. For example, steps A-B of FIG. 1 illustrate an example of attaching an aptamer (2) to a solid support (10) and recognizing ligand, e.g. free EGFR, in a sample. Once the ligand is captured by the aptamer, the ligand in the aptamer-ligand complex (5) is incubated with a detectably labeled binding agent (not shown in FIG. 1) to detect the ligand. Binding agents for detection can include detectably labeled aptamers or antibodies that recognize any epitope of the aptamer-bound free EGFR.

Alternatively, the aptamer-bound ligand (2) can be labeled with a binding pair member (7), e.g. biotin, as illustrated in part C of FIG. 1, and the binding pair member can be detected with a detectably labeled binding agent, e.g. streptavidin or an antibody that recognizes biotin.

Aptamers can also be used to detect analytes in a single-support sandwich assay. For example, referring to step B of FIG. 1, a binding pair member (14), e.g. an antibody, that recognizes only free EGFR in a sample can be attached to a solid support (10) and used to capture EGFR in a sample. A detectably labeled aptamer that recognizes only free EGFR can then be used to detect only the free EGFR in the sample (e.g. aptamer labeled with Alexa Fluor 488-7-OBEA-dCTP; Life Technologies Cat. No. C21555).

Aptamer Modification

Nucleotides in aptamers can be chemically modified, singly or in any combination. Nucleotide chemical modifications in aptamers may include, for example, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium)propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine), modifications at exocyclic amines, substitution of 4-thiouridine, substitution of 5-bromo- or 5-iodo-uracil, backbone modifications, methylations, unusual base-pairing combinations such as the isobases, isocytidine and isoguanidine, and the like.

Figure 5:
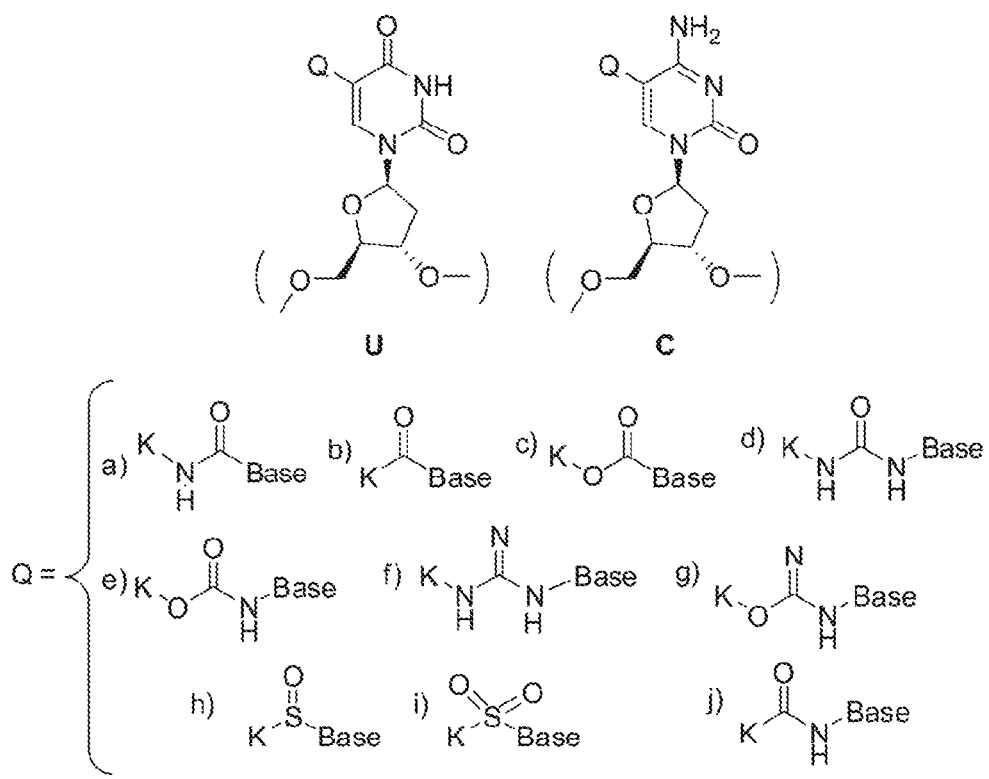
FIG. 5 illustrates C-5 modified pyrimidines which may be used in the aptamers described herein.
Figure 5:
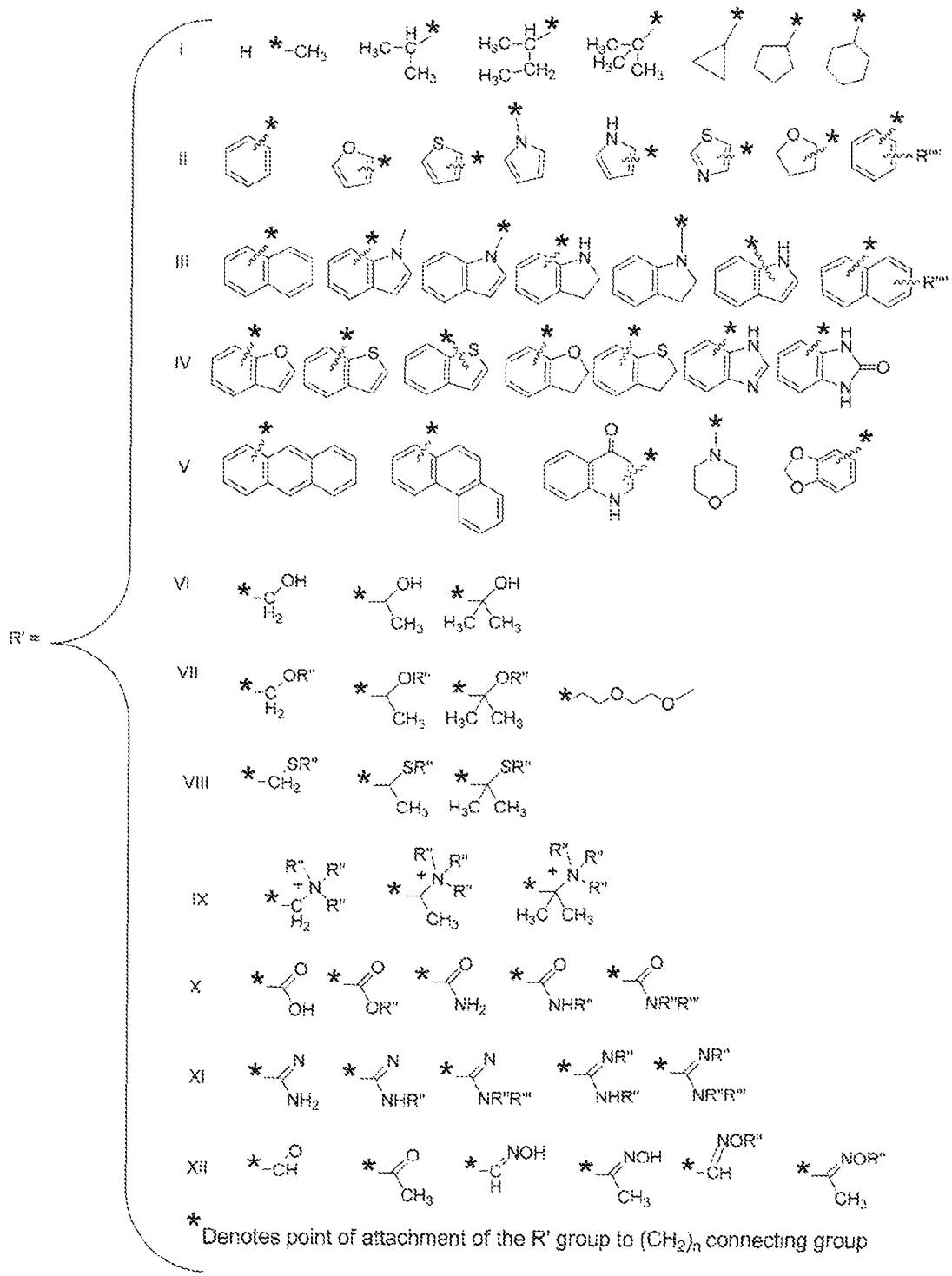

In some embodiments, the term "C-5 modified pyrimidine" refers to a pyrimidine with a modification at the C-5 position including, but not limited to, those moieties shown in FIG. 5. Examples of a C-5 modified pyrimidine include those described in U.S. Pat. Nos. 5,719,273 and 5,945,527. Examples of a C-5 modification include substitution of deoxyuridine at the C-5 position with a substituent selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), isobutylcarboxyamide (alternatively isobutylaminocarbonyl) (iBu), tyrosylcarboxyamide (alternatively tyrosylaminocarbonyl) (Tyr), 2-naphthylmethylcarboxyamide (alternatively 2-naphthylmethylaminocarbonyl) (2Nap) and phenethyl-1-carboxyamide (alternatively phenethyl-1-aminocarbonyl) (PE), as illustrated immediately below.

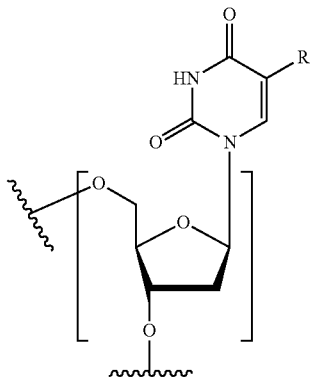

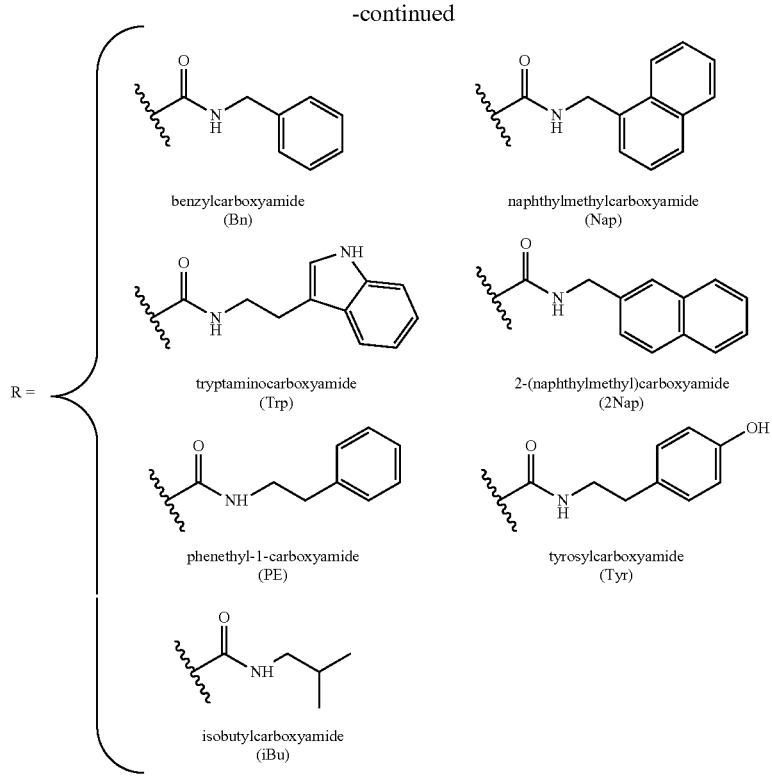

Aptamer modifications may include nucleotide additions or modifications at the 3' and 5' ends, such as a cap or pegylation. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. If present, a modification to the nucleotide structure may be imparted before or after assembly of a polymer. A sequence of nucleotides may be interrupted by non-nucleotide components. A polynucleotide may be further modified after polymerization, such as by conjugation with a labeling component.

Inverted nucleotides may be used as cap on the 3' or 5' end of a nucleic acid. As used herein, the term "inverted nucleotide" means deoxyribonucleotides or ribonucleotides having an orientation opposite to that of the sequence that contains them. Classically, with synthesis taking place in the 3' to 5' direction, inverted nucleotides are introduced following or before the rest of the nucleotide strand, in the 5' to 3' direction. The inverted nucleotides and the rest of the strand are then joined together by a 5'-5' or 3'-3' bond. Reference may be made to Koga M., et al., J. Org. Chem., 1991, 56, 3757. The inverted nucleotides can optionally include at least one modified nucleotide, for example at least one nucleotide having a modified nucleic acid base, such as inosine, methyl-5-deoxycytidine, dimethylamino-5-deoxyuridine, deoxyuridine, diamino-2,6-purine, bromo-5-deoxyuridine or any other modified base permitting hybridization.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R', P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

In some embodiments, an aptamer has the nucleic acid sequence of SEQ ID NO: 1, in which each "N" is, independently, a 5-position modified 2'-deoxyuridine including but not limited to, for example, 5-benzylaminocarbonyl-2'-deoxyuridine, 5-(N-benzylcarboxamide)-2'-deoxyuridine, 5-(N-isobutylcarboxamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine.

(SEQ ID NO: 1)
ANCGAGGNNGNGGGNCGGANNGNNGGANNCNNNAAGNNGGGAACACCA

ACCGAGAACG

In some embodiments, an aptamer includes the nucleic acid sequence of SEQ ID NO: 2, in which each "N" is, independently, a 5-position modified 2'-deoxyuridine including but not limited to, for example, 5-benzylaminocarbonyl-2'-deoxyuridine, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine.

(SEQ ID NO: 2)
NNGNNGGANNCNNNAAG

In some embodiments, an aptamer includes the nucleic acid sequence of SEQ ID NO: 5, in which each "N" is, independently, a 5-position modified 2'-deoxyuridine including but not limited to, for example, 5-benzylaminocarbonyl-2'-deoxyuridine, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine.

(SEQ ID NO: 5)
ANCGAGGNNGNGGGNCGGANNGNNGGANNCNNNAAGNNGGGAACACCAAC

In some embodiments, an aptamer includes the nucleic acid sequence of SEQ ID NO: 6, in which each "N" is, independently, a 5-position modified 2'-deoxyuridine including but not limited to, for example, 5-benzylaminocarbonyl-2'-deoxyuridine, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine.

(SEQ ID NO: 6)
ANCGAGGNNGNGGGNCGGANNGNNGGANNCNNNAAGNNGG

In some embodiments, an aptamer includes the nucleic acid sequence of SEQ ID NO: 7, in which each "N" is, independently, a 5-position modified 2'-deoxyuridine including but not limited to, for example, 5-benzylaminocarbonyl-2'-deoxyuridine, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine.

(SEQ ID NO: 7)
GAGNNGNANGGGGNCGGANNGNNGGANNCNNNAAGNNCGG

In some embodiments, an aptamer includes the nucleic acid sequence of SEQ ID NO: 8, in which each "N" is, independently, a 5-position modified 2'-deoxyuridine including but not limited to, for example, 5-benzylaminocarbonyl-2'-deoxyuridine, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine.

(SEQ ID NO: 8)
GGGNCGGANNGNNGGANNCNNNAAGNN

In some embodiments, the present disclosure provides an aptamer that specifically binds to EGFR and includes a primary nucleic acid sequence. In one embodiment, the primary nucleic acid sequence is selected from SEQ ID NOS: 1 to 8. In other embodiments, the primary nucleic acid sequence is selected such that it is at least 75% identical, at least about 80% identical, at least about 85% identical, at least about 90% percent identical, at least about 91% identical, at least about 92% identical, at least about 93% identical, at least about 94% identical, or at least about 95% identical to a primary nucleic acid sequence selected from SEQ ID NOS: 1 to 8.

The terms "sequence identity", "percent sequence identity", "percent identity", "% identical", "% identity", and variations thereof, when used in the context of two nucleic acid sequences, are used interchangeably to refer to the number of nucleotide bases that are the same in a query nucleic acid or a portion of a query nucleic acid, when it is compared and aligned for maximum correspondence to a reference nucleic acid, divided by either (1) the number of nucleotide bases in the query sequence between and including the most 5' corresponding (i.e., aligned) nucleotide base and the most 3' corresponding (i.e., aligned) nucleotide base, or (2) the total length of the reference sequence, whichever is greater. Exemplary alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M., et al., Current Protocols in Molecular Biology, pub. by Greene Publishing Assoc. and Wiley-Interscience (1987)).

One example of an algorithm that is suitable for determining percent sequence identity is the algorithm used in the basic local alignment search tool (hereinafter "BLAST"), see, e.g. Altschul, et al., J. Mol. Biol. 215:403-410, 1990 and Altschul, et al., Nucleic Acids Res., 15:3389-3402, 1997. Software for performing BLAST analyses is publicly available through the National Center for Biotechnology Information (hereinafter "NCBI"). The default parameters used in determining sequence identity using the software available from NCBI, e.g., BLASTN (for nucleotide sequences) are described in McGinnis, et al., Nucleic Acids Res., 32:W20-W25, 2004.

As used herein, when describing the percent identity of a nucleic acid, such as a EGFR aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence. Further, it is intended that a nucleotide base is considered "identical" for the purposes of determining percent identity, when the nucleotide base (1) is the same as the nucleotide base in the reference sequence, or (2) is derived from the nucleotide base in the reference sequence, or (3) is derived from the same nucleotide base from which the nucleotide base in the reference sequence is derived. For example, 5-methyl cytosine is considered to be "identical" to cytosine for the purposes of calculating percent identity. Similarly, the modified uridines shown in FIG. 5 are considered to be identical to one another for the purpose of determining percent identity. The reference sequence may be any one of the entire nucleotide sequences shown in SEQ ID NOS: 1 to 8, or any fragment of any of these sequences.

Aptamer Labeling

Aptamers may be labeled with a detectable label using several methods known by those having ordinary skill in the art. Signals from the detectable label may be detected by various means and will depend on the nature of the detectable label. Detectable labels include but are not limited to fluorophores, isotopes (e.g., $^{32}P$, $^{33}P$, $^{35}S$, $^{3}H$, $^{14}C$, $^{125}I$, $^{131}I$), electron-dense reagents (e.g., gold, silver), nanoparticles, enzymes commonly used in an ELISA (e.g., horseradish peroxidase, beta-galactosidase, luciferase, alkaline phosphatase), chemiluminescent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

Detectable labels may be incorporated into nucleic acids by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3™ or Cy5™ and then incorporated into nucleic acid probes during nucleic acid synthesis or amplification. Nucleic acid probes may be labeled when synthesized using Cy3™- or Cy5™-dCTP conjugates mixed with unlabeled dCTP.

For example, fluorescently-labeled nucleotides are commercially available and may be enzymatically incorporated into oligonucleotides (e.g. ChromaTide™ nucleotides from Life Technologies/Invitrogen, described in The Molecular Probes Handbook, 11$^{th}$ Edition, section 8.2). In another exemplary method, amine-reactive nucleotides may be incorporated into an oligonucleotide and then amine-reacted with a desired fluorophore (e.g. ARES™ Nucleic Acid Labeling Kits from Life Technologies/Invitrogen, described in The Molecular Probes Handbook, 11$^{th}$ Edition, section 8.2). Another method of labeling oligonucleotides utilizes a platinum-based chemistry system to link molecules with guanine-based nucleotides (e.g. ULYSIS™ Nucleic Acid Labeling Kits from Life Technologies/Invitrogen, described in The Molecular Probes Handbook, 11$^{th}$ Edition, section 8.2).

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulfur containing side chains of amino acids. See, e.g., U.S. Pat. Nos. 5,580,990; 5,714,327; and 5,985,566; and European Patent No. 0539466.

Labeling with a detectable label also may include nucleic acid probes attached to another biological molecule, such as a nucleic acid, e.g., an oligonucleotide, or a nucleic acid in the form of a stem-loop structure as a "molecular beacon" or an "aptamer beacon". Molecular beacons as detectable moieties are well known in the art; for example, Sokol (Proc. Natl. Acad. Sci. USA (1998), 95:11538-11543) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (Biochemistry (2001), 40:9387-9395), describing a molecular beacon consist of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, Anal. Biochem. (2001), 294:126-131; Poddar, Mol. Cell. Probes (2001), 15:161-167; Kaboev, Nucleic Acids Res. (2000), 28:E94. Aptamer beacons may adopt two or more conformations, one of which allows ligand binding. A fluorescence-quenching pair is used to report changes in conformation induced by ligand binding. See also, e.g., Yamamoto, et al., Genes Cells (2000), 5:389-396; Smirnov, et al., Biochemistry (2000), 39:1462-1468.

The nucleic acid probe may be indirectly detectably labeled via a peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). A label may also be attached via a second peptide that interacts with the first peptide (e.g., S—S association).

Solid Supports

A solid support may take any of a variety of configurations ranging from simple to complex. The solid support can have anyone of a number of shapes, including a strip, plate, disk, rod, particle, bead, tube, well (microtiter), and the like. The solid support may be porous or non-porous, magnetic, paramagnetic, or non-magnetic, polydisperse or monodisperse, hydrophilic or hydrophobic. The solid support may also be in the form of a gel or slurry of closely-packed (as in a column matrix) or loosely-packed particles.

The material of a solid support is generally capable of enduring conditions related to the attachment of the binding pair members or probes to the surface and any subsequent treatment, handling, or processing encountered during the performance of an assay. The materials may be naturally occurring, synthetic, or a modification of a naturally occurring material. Suitable solid support materials may include silicon, a silicon wafer chip, graphite, mirrored surfaces, laminates, membranes, ceramics, plastics (including polymers such as, e.g., latex, poly(vinyl chloride), cyclo-olefin copolymers, agarose gels or beads, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, Langmuir Blodgett films, a flow through chip, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads, crosslinked beaded Sepharose® or agarose resins, or copolymers of crosslinked bis-acrylamide and azalactone. Other beads include polymer beads, solid core beads, paramagnetic beads, or microbeads. Any other materials known in the art that are capable of having one or more functional groups, such as any of an amino, carboxyl, thiol, or hydroxyl functional group, for example, incorporated on its surface, are also contemplated.

Non-Covalent Attachment of Aptamers to a Solid Support

Aptamer constructs can be attached to a solid support non-covalently using one binding pair member attached to a solid support (covalently or non-covalently) and one binding pair member attached to the aptamer. Binding pairs include biotin and streptavidin, antibody and antigen, the Fab region of an antibody and its antigen, protein A and the Fc domain of IgG, and a single oligonucleotide strand and its complement.

In some embodiments, the binding pair for attaching the aptamer is biotin and streptavidin, wherein the aptamer is biotinylated and the solid support is coated with streptavidin. Methods for biotinylating nucleic acid are known in the art (e.g. by photo-cross linking using EZ-link psoralen-PEO biotin from Pierce Chemical Co., by chemical coupling using Label IT® µArray® Biotin Labeling Kit from Minis Bio Corp., PFP Biotin from Pierce Chemical Co., by nick translation using BioNick DNA Labeling System from Invitrogen corporation, or by 3'-end labeling using commercially available kits e.g. Biotin 3-end labeling kit from Pierce).

In other embodiments, the binding pair consists of a ligand-receptor, a hormone-receptor, and an antigen-antibody. Examples of such binding pair include but are not limited to digoxigenin and anti-digoxigenin antibody; 6-(2,4-dinitrophenyl)aminohexanoic acid and anti-dinitrophenyl antibody; 5-Bromo-dUTP (BrdUTP) and anti-BrdUTP antibody; N-acetyl 2-aminofluorene (AAF) and anti-AAF antibody. The solid surfaces in these cases consist of the antibody, and the genomic nucleic acid is modified to consist of the antigen. Methods of incorporating digoxigenin, 2,4-dinitrophenyl group, 5-Bromo-dUTP group into DNA can be achieved by nick translation, or by terminal transferase reaction, examples of which are amply documented in the art or may be achieved by using commercially available kits e.g. kits DIG DNA labeling kit from Roche Applied Sciences. Digoxigenin can be chemically coupled to the nucleic acid with Digoxigenin-NHS-ester. N-acetyl 2-aminofluorene (AAF) can be covalently coupled to the genomic nucleic acid.

Covalent Attachment of Aptamers to a Solid Support

Aptamer can also be covalently attached to a solid support using functionalization chemistry for creating microarrays or nucleotide-coated beads. If covalent bonding between the genomic nucleic acid and the surface is desired, the solid surface will usually be functional or be capable of being functionalized. Examples of functional groups used for linking include but are not limited to carboxylic acids, aldehydes, amino groups, cyano groups, ethylenic groups, hydroxyl groups, thiol groups.

For example, methods for synthesizing oligonucleotides from nucleic acids attached to solid supports have been described (see, e.g., U.S. Pat. No. 5,436,327, U.S. Pat. No. 5,800,992, U.S. Pat. No. 5,445,934, U.S. Pat. No. 5,763,170, U.S. Pat. No. 5,599,695 and U.S. Pat. No. 5,837,832). Solid supports can also be thiol- or amine-functionalized and then reacted with an oligonucleotide having the properly modified nucleic acid.

In some embodiments, the solid support may be coated with epoxy group, amino group, mercapto group, or polylysine. Coated solid supports are available commercially e.g. beads coated with functional groups are available from Invitrogen Corporation, BD Biosciences; glass slides coated with functional groups are available from Pierce, Asper Biotech, Full Moon Biosystems, and ThermoFisher Inc.

The aptamer may be modified to consist of functional groups. The 5' phosphate group of genomic nucleic acid, may be conjugated to primary amine-containing molecules using the carbodiimide crosslinker EDC (Pierce Product No. 22980) and imidazole. The 5' phosphate group of a nucleic acid may be modified to consist of amine group with an excess of ethylenediamine, and using carbodiimide crosslinker EDC (Pierce Product No. 22980) and imidazole as described in Pierce Technote No. 30. Depending on the amine containing molecules used, the crosslinking strategy can be adapted in a number of ways to directly or indirectly modify, label or conjugate genomic nucleic acid. For example, to create a photoactivable (random-reactive) nucleic acid, p-azidobenzoyl hydrazide, (ABH, Pierce catalog No. 21510) may be used instead of ethylenediamine in the default reaction. To create a sulfhydryl-reactive nucleic acid, [N-e-Maleimidocaproic acid]hydrazide, trifluoroacetic acid salt (EMCH, Pierce catalog No. 22106), N-[k-Maleimidoundecanoic acid]hydrazide, (KMUH Pierce catalog No. 22111), or 4-(4-N-Maleimidophenyl)butyric acid hydrazide hydrochloride, (MPBH Pierce catalog No. 22305) may be used instead of ethylenediamine in the default reaction. To obtain a sulfhydryl crosslink that is reversible 3-(2-Pyridyldithio) propionyl hydrazide (PDPH, Pierce catalog No. 22301) may be used instead of ethylenediamine. This strategy is useful for linking genomic nucleic acid to sulfhydryl-containing solid support. To create a sulfhydryl group on genomic nucleic acid cystamine ($NH_2$—$CH_2$—$CH_2$—S—S—$CH_2$—$CH_2$—$NH_2$) may be used instead of ethylenediamine in the default reaction, and then reduce the disulfide bond with DTT or similar reagent. This strategy is useful for covalently coupling to maleimide activated solid support. To immobilize nucleic acid to a beaded affinity support, UltraLink Hydrazide (Pierce catalog No. 53149) may be used instead of ethylenediamine in the default reaction.

The manner of linking a wide variety of functional groups to each other is well known and is amply illustrated in the literature. In one embodiment, the chemical linkers may be used to covalently link two functional groups, one on the solid support and the other on the genomic nucleic acid. The chemical linkers may be mono functional, bifunctional, polyfunctional, hetero-bifunctional, or hetero-polyfunctional. In some embodiments, the chemical linkers may have spacer arms to avoid steric hindrance. Examples of chemical linkers to couple amino group to an amino group include but are not limited to ethylene glycol bis[succinimidylsuccinate], disuccinimidyl suberate, 1,5-difluoro-2,4-dinitrobenzene. Examples of chemical linkers to couple thiol group to a thiol group include but are not limited to 1,4-di-[3'-(2'-pyridyldithio)-propionamido]butane, dithio-bismaleimidoethane. A wide variety of suitable cross linkers and the methods of cross linking are available from Pierce.

In another embodiment, the genomic nucleic acid is anchored to the solid support through photoactive moieties. In one embodiment, the solid surface may anchor photoactive moieties capable of coupling the genomic nucleic acid by photo activation. In another embodiment, the 5' phosphate group of genomic nucleic acid may be conjugated to a photoactive group, capable of photocrosslinking to functional groups on the solid surface. In another embodiment, the genomic nucleic acid may be anchored to the solid surface through a linker having two or more photoactive moieties, one or more at each end, wherein the linker couples to the solid surface and to the genomic nucleic acid upon exposing the solid surface and genomic nucleic acid in presence of the linker with radiation of suitable wavelength. Examples of photoactive moieties include but not limited to azides, aryl azides, azidophenacyl, 4-nitrophenyl 3-diazopyruvate, psolarens, psolaren derivatives.

In another embodiment, the aptamer can be cross-linked to nylon, nitrocellulose, or nylon-reinforced nitrocellulose membranes, by exposing the solid surface and the nucleic acid to ultra-violet radiation. The manner of cross-linking linking of nucleic acid to various surfaces is well known and is amply illustrated in the literature (e.g. using Stratagene UV crosslinker).

Aptamer Amplification

Nucleic acid aptamers may be amplified by various methods known to the skilled artisan. Nucleic acid amplification may be linear or exponential. Amplification is generally carried out using polymerase chain reaction (PCR) technologies known in the art. See e.g., Mullis and Faloona, Methods Enzymol. (1987), 155:335, U.S. Pat. Nos. 4,683,202, 4,683, 195 and 4,800,159.

Oligonucleotide tags may be used to detect and identify aptamers. For example, a known unique sequence of nucleic acids can be added to the 5' or 3' end of an aptamer that can be identified using PCR techniques known in the art. The tag may be recognized by primers used to amplify the aptamer Alternative methods to PCR include for example, isothermal amplification methods, rolling circle methods, Hot-start PCR, real-time PCR, Allele-specific PCR, Assembly PCR or Polymerase Cycling Assembly (PCA), Asymmetric PCR, Colony PCR, Emulsion PCR, Fast PCR, Real-Time PCR, nucleic acid ligation, Gap Ligation Chain Reaction (Gap LCR), Ligation-mediated PCR, Multiplex Ligation-dependent Probe Amplification, (MLPA), Gap Extension Ligation PCR (GEXL-PCR), quantitative PCR (Q-PCR), Quantitative real-time PCR (QRT-PCR), multiplex PCR, Helicase-dependent amplification, Intersequence-specific (ISSR) PCR, Inverse PCR, Linear-After-The-Exponential-PCR (LATE-PCR), Methylation-specific PCR (MSP), Nested PCR, Overlap-extension PCR, PAN-AC assay, Reverse Transcription PCR (RT-PCR), Rapid Amplification of cDNA Ends (RACE PCR), Single molecule amplification PCR (SMA PCR), Thermal asymmetric interlaced PCR (TAIL-PCR), Touchdown PCR, long PCR, nucleic acid sequencing (including DNA sequencing and RNA sequencing), transcription, reverse transcription, duplication, DNA or RNA ligation, and other nucleic acid extension reactions known in the art. The skilled artisan will understand that other methods may be used either in place of, or together with, PCR methods, including enzymatic replication reactions developed in the future. See, e.g., Saiki, "Amplification of Genomic DNA" in PCR Protocols, Innis, et al., eds., Academic Press, San Diego, Calif., 13-20 (1990); Wharam, et al., 29(11) Nucleic Acids Res, E54-E54 (2001); Hafner, et al., 30(4) Biotechniques, 852-6, 858, 860 passim (2001).

Detection of Amplified Aptamer

Amplification of nucleic acid aptamers can be detected by any of a number of methods well-known in the art such as gel electrophoresis, column chromatography, hybridization with a probe, or sequencing.

One general method for real time PCR uses fluorescent probes such as the TaqMan® probes (Heid, et al., Genome Res 6: 986-994, 1996), molecular beacons, and Scorpions™. Real-time PCR quantifies the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

Suitable fluorescent moieties include but are not limited to the following fluorophores working individually or in combination:
4-acetamido-4'-isothiocyanatostilbene-2,2'-disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'- disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DAB CYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4',5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY® 7; QSY® 9; QSY® 21; QSY® 35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC).

Molecular beacons as detectable moieties are well known in the art; for example, Sokol (Proc. Natl. Acad. Sci. USA (1998), 95:11538-11543) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (Biochemistry (2001), 40:9387-9395), describing a molecular beacon consist of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, Anal. Biochem. (2001), 294:126-131; Poddar, Mol. Cell. Probes (2001), 15:161-167; Kaboev, Nucleic Acids Res. (2000), 28:E94. Aptamer beacons can adopt two or more conformations, one of which allows ligand binding. A fluorescence-quenching pair is used to report changes in conformation induced by ligand binding. See also, e.g., Yamamoto, et al., Genes Cells (2000), 5:389-396; Smirnov, et al., Biochemistry (2000), 39:1462-1468.

Detection of Nucleic Acid Aptamer by Size

Methods for detecting the presence or amount of nucleic acid are well known in the art and any of them can be used in the methods described herein so long as they are capable of separating individual nucleic acid by the difference in size of the amplicons. The separation technique used should permit resolution of nucleic acid as long as they differ from one another by at least one nucleotide. The separation can be performed under denaturing or under non-denaturing or native conditions—i.e., separation can be performed on single- or double-stranded nucleic acids. It is preferred that the separation and detection permits detection of length differences as small as one nucleotide. It is further preferred that the separation and detection can be done in a high-throughput format that permits real time or contemporaneous determination of amplicon abundance in a plurality of reaction aliquots taken during the cycling reaction. Useful methods for the separation and analysis of the amplified products include, but are not limited to, electrophoresis (e.g., agarose gel electrophoresis, capillary electrophoresis (CE)), chromatography (HPLC), and mass spectrometry.

Detection of Nucleic Acid Aptamer by Sequencing

In some examples, detection of nucleic acid is by sequencing. Sequencing may be carried out by the dideoxy chain termination method of Sanger, et al. (Proceedings of the National Academy of Sciences USA (1977), 74, 5463-5467) with modifications by Zimmermann, et al. (Nucleic Acids Res. (1990), 18:1067). Sequencing by dideoxy chain termination method can be performed using Thermo Sequenase (Amersham Pharmacia, Piscataway, N.J.), Sequenase reagents from US Biochemicals or Sequatherm sequencing kit (Epicenter Technologies, Madison, Wis.). Sequencing may also be carried out by the "RR dRhodamine Terminator Cycle Sequencing Kit" from PE Applied Biosystems (product no. 403044, Weiterstadt, Germany), Taq DyeDeoxy™ Terminator Cycle Sequencing kit and method (Perkin-Elmer/Applied Biosystems) in two directions using an Applied Biosystems Model 373A DNA or in the presence of dye terminators CEQ™ Dye Terminator Cycle Sequencing Kit, (Beckman 608000). Alternatively, sequencing can be performed by a method known as Pyrosequencing (Pyrosequencing, Westborough, Mass.). Detailed protocols for Pyrosequencing can be found in: Alderbom, et al., Genome Res. (2000), 10:1249-1265.

Detecting Free EGFR in a Patient Sample

Epithelial carcinomas are the most common type of cancer in humans, as epithelial cells are found in organs throughout the body. Carcinomas can develop from squamous cells in organ linings (e.g. skin, lips, mouth, esophagus, bladder, prostate, lung, ovaries, uterus, vagina, cervix, or colon), from adenomatous cells in glands (adenocarcinomas, e.g. lung, prostate, urachus, ovaries, uterus, vagina, breast, esophagus, thyroid, parathyroid, pancreas, or stomach), or from transitional cells (e.g. kidney, bladder, ovaries, prostate, uterus, cervix, ureter, urethra, or urachus). Epithelial carcinomas also occur in brain tissues such as the choroid plexus.

The extracellular domain of EGFR is shed in both healthy people as well as patients with ovarian, lung, bladder, prostate, breast, and colon cancer (Carney, Expert Rev Mol Diagn. 2007 May; 7(3):309-19), and serum levels of EGFR in patients with cancer are known to vary from EGFR levels measured in healthy controls. For example, serum EGFR levels (extracellular domain) in patients with head and neck cancer, NSCLC, breast cancer, ovarian cancer, colon cancer, bladder cancer, and prostate cancer have been shown to be lower than those in healthy controls. In contrast, serum EGFR levels in pancreatic, thyroid, cervical, gastric and pituitary carcinomas are higher than in healthy controls (Lemos-Gonzalez, et al., Br J Cancer. 2007 May 21; 96(10):1569-78). Furthermore, some patients have cancer that is resistant or becomes resistant to treatment with cetuximab or panitumumab (see Carney, Expert Rev Mol Diagn. 2007 May; 7(3): 309-19; Wheeler, et al., Oncogene. 2008 Jun. 26; 27(28): 3944-3956; Bardelli, et al., J Clin Oncol. 2010 Mar. 1; 28(7): 1254-61).

Monitoring levels of free EGFR in samples from cancer patients receiving treatment with therapeutic molecules that bind EGFR (e.g. cetuximab or panitumumab) can provide information about the cancer's response to treatment. By comparing the amount of free EGFR relative to bound EGFR in a patient being treated with a therapeutic EGFR-binding molecule, a treatment provider can determine whether the therapeutic EGFR-binding molecule is binding sufficient amounts of free EGFR to effectively treat that particular cancer. A cancer patient being treated with a therapeutic EGFR-binding molecule can be monitored at various time points during the course of treatment for possible changes in the amount of free EGFR relative to bound EGFR. Such changes can indicate that the cancer is responding to the treatment or becoming resistant to the treatment.

Identification of Consensus Sequence

A SELEX experiment was run in which approximately 1425 sequences to EGFR were isolated. FIG. 10 sets forth the number of unique sequences identified including the number of copies of each sequence. With reference to FIG. 10, it can be seen that 21 unique sequences were isolated. FIG. 10 shows the alignment of the 21 sequences relative to each other. FIG. 11 summarizes the consensus sequence as a frequency matrix in (1) unique counts and (2) total copy counts. From this information the following consensus sequence was identified:

```
                                              (SEQ ID NO: 55)
XGANNGNNYGANNCNN;
``` wherein X is G, C, or A; Y is G or A and each "N" is, independently, a 5-position modified 2'-deoxyuridine including but not limited to, for example, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl] carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine. Many of these nucleotide modifications are anticipated to be equally effective in promoting high affinity binding to the EGF Receptor (EGFR) and providing a slow off rate.

Thus in one aspect, with reference to FIGS. 10 and 11 the present disclosure includes an aptamer to the EGF Receptor selected from:

```
                                              (SEQ ID NO: 55)
XGANNGNNYGANNCNN;
``` wherein X is G, C, or A; Y is G or A and each "N" is, independently, a 5-position modified 2'-deoxyuridine including but not limited to, for example, 5-benzylaminocarbonyl-2'-deoxyuridine, 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine. In one embodiment each "N" is a 5-(N-benzylcarboxyamido)-2'-deoxyuridine.

In some aspects, N is further modified at the 2'-position with a moiety selected from the group including, but not limited to for example 2'-O-methyl-, 2'-O-allyl, 2'-fluoro- or 2'-azido-ribose, etc. as described above.

In another embodiment, the present disclosure provides an aptamer that specifically binds to the EGF Receptor, wherein the primary nucleic acid sequence is selected SEQ ID NOS: 1-54. In other embodiments, the primary nucleic acid sequence is selected such that it is at least about 50% identical, at least about 60% identical, at least about 70% identical, at least about 75% identical, at least about 80% identical, at least about 85% identical, at least about 90% identical, or at least about 95% identical to a primary nucleic acid sequence selected from SEQ ID NOS: 1-55.

In further embodiments, the present disclosure provides an aptamer that specifically binds to the EGF Receptor, wherein the primary nucleic acid sequence includes a sequence of contiguous nucleotides that are identical to a sequence of contiguous nucleotides included in any of SEQ ID NOS: 34 to 55. For example, in various embodiments, the sequence of contiguous nucleotides in the EGFR aptamer can include a sequence of contiguous nucleotides selected from an nucleic acid which is comprised of at least 6 contiguous nucleotides from the consensus sequence, SEQ ID NO: 55; at least 7 contiguous bases from the consensus sequence; of at least 8 contiguous bases from the consensus sequence; of at least 9 contiguous bases from the consensus sequence; of at least 10 contiguous bases from the consensus sequence; of at least 11 contiguous bases from the consensus sequence; of at least 12 contiguous bases from the consensus sequence; of at least 13 contiguous bases from the consensus sequence; of at least 14 contiguous bases from the consensus sequence; and of at least 15 contiguous bases from the consensus sequence.

The EGFR aptamer can contain any number of nucleotides in addition to the EGFR binding region. In various embodiments, the EGFR aptamer can include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides in addition to the binding region.

EXAMPLES

Example 1

EGFR Aptamer Construct

A nucleic acid aptamer was isolated that only binds EGFR when it is not bound by either of the therapeutic antibodies cetuximab or panitumumab. The aptamer had the nucleic acid sequence of SEQ ID NO: 1, in which each "N" is the modified deoxyuridine, 5-benzylaminocarbonyl-2'-deoxyuridine.

```
                                              (SEQ ID NO: 3)
ANCGAGGNNGNGGGNCGGANNGNNGGANNCNNNAAGNNGGGAAC

ACCAACCGAGAACG
```

A modified aptamer was isolated that only binds EGFR when it is not bound by either of the therapeutic antibodies cetuximab or panitumumab, shown in SEQ ID NO: 4, in which "N" represents a modified deoxyuridine (5-benzylaminocarbonyl-2'-deoxyuridine). The $K_d$ for EGFR of this aptamer was $1.23 \times 10^{-10}$ M.

```
                                              (SEQ ID NO: 4)
CCACGCTGGGTGGGTCANCGAGGNNGNGGGNCGGANNGNNGGAN

NCNNNAAGNNGGGAACACCAACCGAGAACG
```

An aptamer having the nucleic acid sequence of SEQ ID NO: 5, a truncate of SEQ ID NO: 4, was found to have a $K_d$ for EGFR of $5.26 \times 10^{-10}$ M.

An aptamer having the nucleic acid sequence of SEQ ID NO: 6, the 40-mer selected region of SEQ ID NO: 4, also had binding affinity for EGFR.

From the same SELEX pool in which the aptamer having the nucleic acid sequence of SEQ ID NO: 4 was isolated, an aptamer having the nucleic acid sequence of SEQ ID NO: 7 was identified to have binding affinity to EGFR.

The nucleic acid sequence represented by SEQ ID NO: 8 was present in both the aptamer of SEQ ID NO: 4 and the aptamer of SEQ ID NO: 7, representing a consensus sequence present in the two distinct, independently isolated aptamers.

Figure 2:
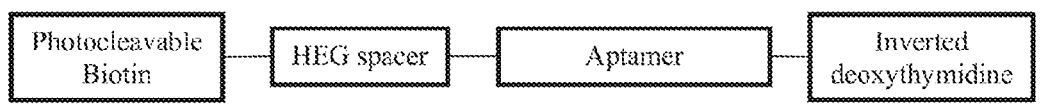
FIG. 2 shows a schematic of an aptamer construct. Details are discussed in Example 1.

The aptamers were then further modified with a hexaethylene glycol (HEG) spacer molecule on the 5' end that connected the aptamer to a photocleavable biotin molecule. The aptamer was also modified with an inverted deoxythymidine on the 3' end. A schematic of the aptamer construct is shown in FIG. 2.

Example 2

Sample Preparation

Serum samples containing EGFR were added to a 96-well plate. Test wells received either cetuximab (Bristol-Meyer NDC 66733-948-23) or panitumumab (Amgen NDC 55513-954-01) at varying concentrations (20 µg/mL, 10 µg/mL, 5 µg/mL, 1 µg/mL, 0.5 µg/mL, 0.05 µg/mL, control with no antibody). A negative control antibody at 60 µg/mL was also prepared. Serum standards lacking the therapeutic antibodies and with various concentrations of exogenous EGFR were also prepared (1000 pM, 200 pM, 40 pM, 8 pM, 1.6 pM, 0.32 pM, and 0.06 pM of EGFR). All dilutions of antibodies, serum, and EGFR standards were made with SB 17T buffer.

Example 3

Aptamer-EGFR Complex Formation and Partitioning from Sample

The aptamer of SEQ ID NO: 4 modified as in FIG. 2 was added to antibody-spiked serum samples and standards as described in Example 2 to a final concentration of 1 nM. The 96-well plate was incubated for 3 hours at 37° C. to achieve equilibrium binding between EGFR in the sample and the aptamer. The serum sample/aptamer mixture from each well was transferred to a streptavidin-coated 96 well plate and incubated for 30 minutes at 37° C. with shaking at 400 rpm.

Example 4

Biotin Labeling of EGFR in Complex

Patient samples were prepared, mixed, and partitioned on a 96-well plate as described in Example 3. Following the streptavidin incubation, the plate was washed with PB1T buffer containing 1 mM dextran sulfate and 500 µM biotin to saturate any unbound streptavidin, and then washed with PB1T.

Next, 1 mM NHS-PEG4-Biotin (diluted in PB1T pH 7.25) was added to the plate and incubated for 5 minutes at room temperature while being shaken at 600 rpm. The plate was then washed with 20 mM glycine in PB1T, and then with PB1T.

Example 5

Partitioning of Aptamer-EGFR Complex from Unbound Aptamer

Patient samples were prepared, mixed, and partitioned from the sample as described in Examples 1-3, and the aptamer-EGFR complex was bound to the plate and the EGFR was biotinylated as described in Example 4. Next, the plate wells were exposed to 1 mM dextran sulfate in PB1 buffer, exposed to UV light, and shaken for 5 minutes while shaking at 600 rpm.

The supernatant was then removed from the plate and added to another streptavidin-coated 96-well plate (previously washed in NaOH) and incubated for 10 minutes at room temperature with shaking. The plate was then washed with 50% PG in PB1T buffer, and then in PB1T buffer.

Example 6

Removal of Aptamer from Plate-Bound EGFR

Patient samples were prepared, mixed, and partitioned from the sample as described in Examples 1-3. The aptamer-EGFR complex was bound to the plate, the EGFR was biotinylated, and the complex was partitioned from unbound aptamer as described in Examples 4 and 5.

The aptamer was then released from the EGFR by adding CAPSO buffer and incubated for 5 minutes with shaking at 600 rpm. The supernatant was removed to a 96-well plate and neutralization buffer was added to the supernatant to raise the pH.

Example 7

Aptamer Detection and Quantitation

Patient samples were prepared, mixed, and partitioned from the sample as described in Examples 1-3. The aptamer-EGFR complex was bound to the plate and the EGFR was biotinylated, as described in Example 4. Following partitioning of the aptamer-EGFR complex from unbound aptamer as described in Example 5, the aptamer was removed from the plate-bound EGFR as described in Example 6.

The aptamer was then detected using a commercially available xTAG® assay (Luminex Corp., Austin, Tex.). Data was generated by SomaLogic®, Boulder, Co., USA.

Results

Figure 3:
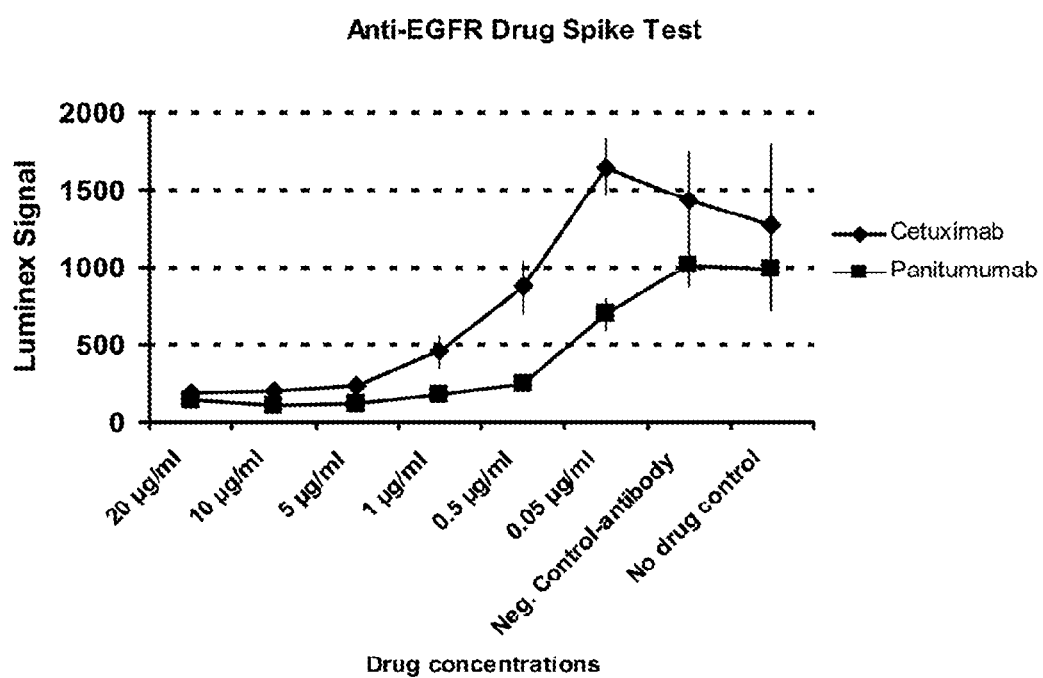
FIG. 3 shows a graph of the fluorescent intensity from a Luminex xTag™ assay for serum samples spiked with successively decreasing amounts of either cetuximab or panitumumab. Data was generated by SomaLogic®, Boulder, Co., USA. Details are discussed in Example 7.

FIG. 3 shows a graph of the fluorescent intensity from a Luminex xTag® assay for serum samples spiked with successively decreasing amounts of either cetuximab or panitumumab. As the concentration of each of the therapeutic antibodies decreases in the spiked samples, the amount of aptamer detected increases. These data show that the aptamer binds EGFR that is not bound to either cetuximab or panitumumab.

Example 8

Development of an Assay Based on SOMAmer Affinity Reagents that Detects Drug-Unbound Serum EGFR in the Presence of Cetuximab and Panitumumab A Slow Off-Rate Modified Aptamer (SOMAmer) targeting the EGFR ECD was selected via Systematic Evolution of Ligands by Exponential Enrichment (SELEX). Using this SOMAmer as a capturing reagent and based on published studies (Gold, et al. PLoS ONE; Dec. 7, 2010:10.1371/journal.pone.0015004), we developed a quantitative serum EGFR assay to reliably quantify EGFR in serum.

Recovery tests using various amounts of purified EGFR spiked into serum demonstrated a full level of EGFR. Intra and inter assay variability were tested and showed minimum variability. The detection range is 0.95 ng/ml to 600 ng/ml.

Interestingly, when serum samples from patients taking cetuximab or panitumumab at the time of blood collection were tested, we observed markedly lower levels of EGFR-captured SOMAmer. ELISA assays from 2 different vendors showed normal to high levels of EGFR in these samples. We further showed that pretreatment of normal serum with either cetuximab or panitumumab can dose-dependently reduce the EGFR SOMAmer signal. The data suggest that our EGFR SOMAmer assay detects serum EGFR molecules that are unbound by cetuximab or panitumumab. Some treated patient samples had more drastic reductions in circulating serum EGFR than others.

Various assay development parameters such as accuracy, detection range, and intra and inter assay variability showed that a SOMAmer-based assay detecting serum EGFR can be used in a clinical setting. Our data suggest that this assay can accurately measure drug-unbound EGFR in patients, which may serve as a surrogate drug efficacy indicator, and this may help physicians to adjust the drug dosage.

Example 9

Further Development of an Assay Based on SOMAmer (Slow Off-Rate Modified Aptamer) Affinity Reagents that Detects Drug-Unbound Serum EGFR in the Presence of Cetuximab and Panitumumab We describe a serum EGFR assay that may provide a means to address the variability in cetuximab and/or panitumumab interaction with EGFR. This assay is based on slow off-rate modified aptamer (SOMAmer™; SomaLogic, Boulder, Colo.) technology (Gold L, Ayers D, Bertino J, et al. Aptamer-based multiplexed proteomic technology for biomarker discovery. *PLoS One.* 2010; 5:e15004.; Kraemer S, Vaught J D, Bock C, et al. From SOMAmer-based biomarker discovery to diagnostic and clinical applications: a SOMAmer-based, streamlined multiplex proteomic assay. PLoS One; 2011; 6:e26332.), which appears to measure circulating EGFR ECD that is not bound by cetuximab or panitumumab.

Patient Samples. Serum samples used for this study were collected from healthy individuals and tested individually (EGFR recovery studies) or as pooled sera (drug interference studies).

SOMAmer Assay. SOMAmers are single-stranded DNA molecules (aptamers) containing modified nucleotides that use their unique secondary structures to create specific and long lasting interactions with their target proteins. SOMAmers are coupled with a biotin moiety via a photo-cleavable linker sequence.

Figure 6:
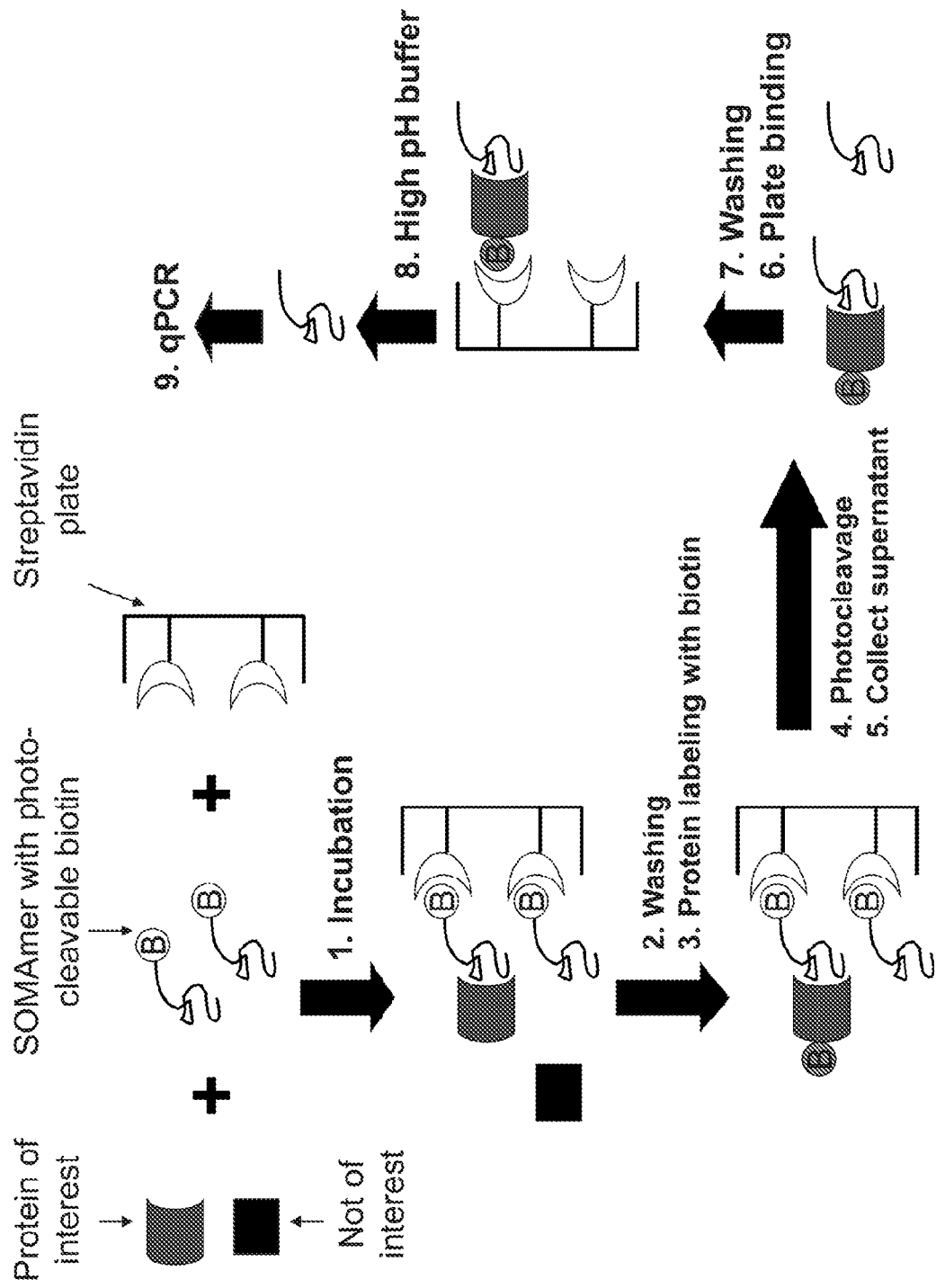
FIG. 6 illustrates the work flow of the aptamer assay.

FIG. 6 describes the work flow of the SOMAmer assay. In brief, diluted serum is incubated with SOMAmers, and the SOMAmers are captured on a streptavidin plate. Proteins not bound to the SOMAmer (non-EGFR proteins) are washed away, and the captured proteins are labeled with another biotin moiety. The plate is then exposed to LED light to break the link between the biotin and aptamer and releases both protein-bound and unbound aptamers. The supernatant is then transferred to a new streptavidin plate allowing this time biotinylated protein-streptavidin interaction, washed to remove protein-unbound aptamer, and exposed to alkaline buffer to release the protein-bound aptamer component, which then serves as the template for quantitative real-time PCR (qPCR).

Figure 7:
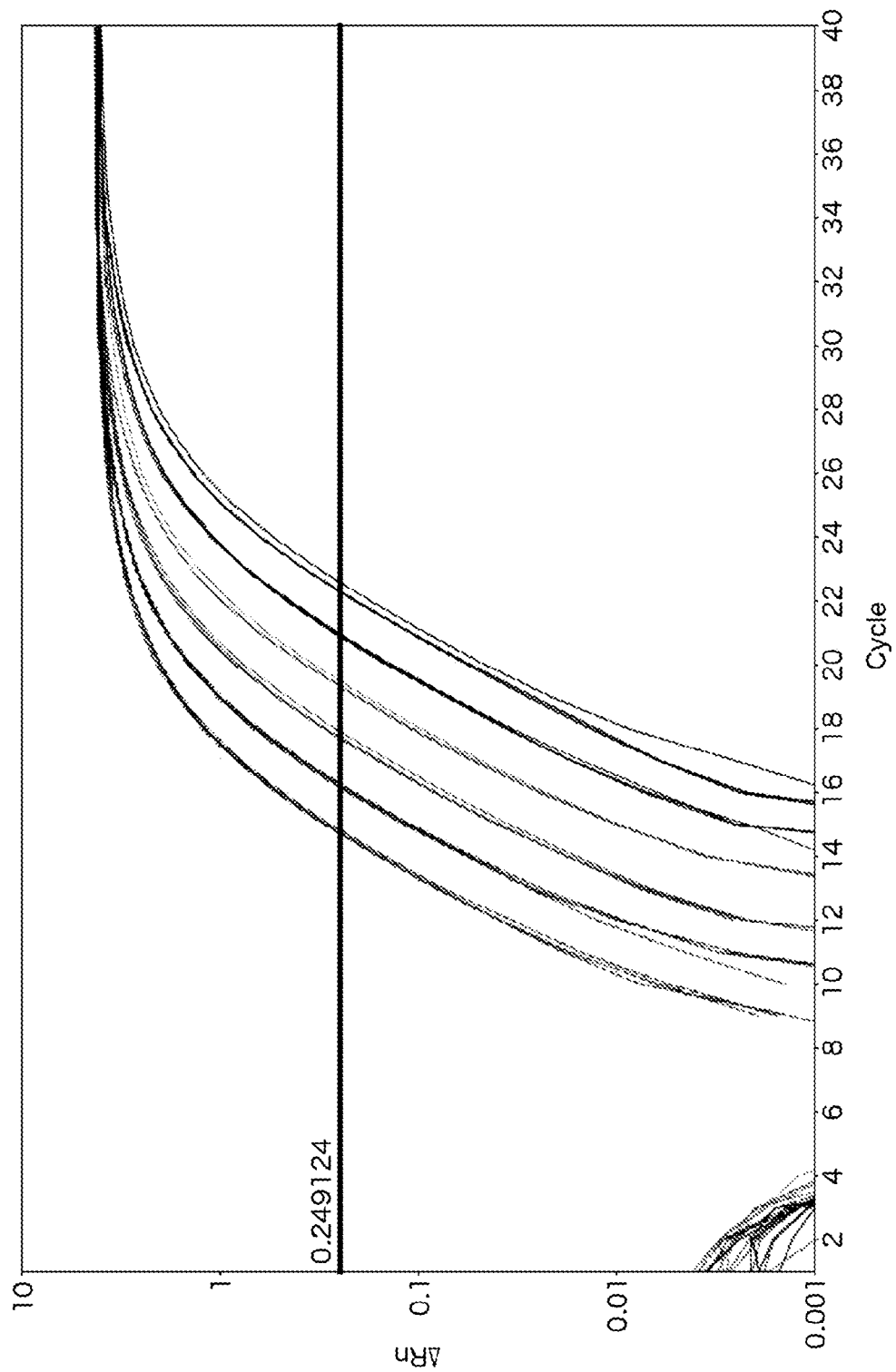
FIG. 7 illustrates representative results of quantitative PCR of serially diluted EGFR-captured SOMAmer.

EGFR qPCR Assay. We used SYBR® green (Life Technologies, Carlsbad, Calif.)-based qPCR. In addition to the Taq DNA polymerase, we also added KOD XL polymerase to enhance readthrough of modified nucleotides. The ABI ViiA 7 instrument (Applied Biosystems, Foster City, Calif.) was used. A typical example of a qPCR using serially diluted EGFR-captured SOMAmer is shown on FIG. 7.

Purified EGFR protein was serially diluted in 3-fold steps from 600 to 2.5 ng/L. Each dilution was further diluted to 30-fold using the SB 17T buffer to mimic the serum dilution. The EGFR SOMAmer assay and qPCR were done as described in the Materials and Methods. Triplicate runs were performed for each dilution.

EGFR ELISA. The EGFR ELISA assay was performed according to the manufacturer's instructions (Wilex, Cambridge, Mass.).

Figure 8:
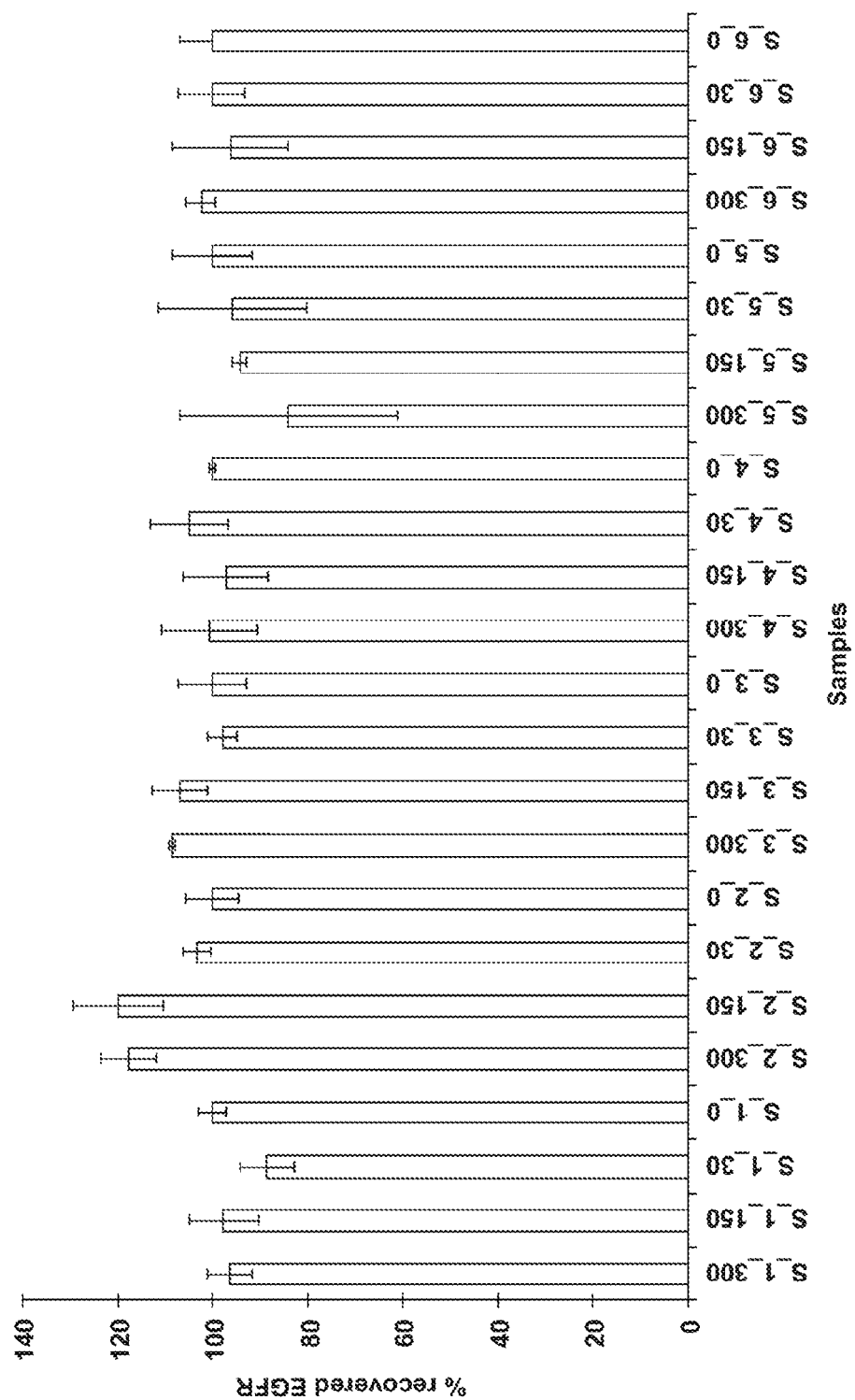
FIG. 8 illustrates recovery studies using varying amounts of purified EGFR spiked into sera of 6 healthy individuals. Bars indicate mean values of triplicate runs; error bars indicate the standard error of the mean.

Recovery studies using serum samples spiked with different levels of purified EGFR (30, 150, and 300 ng/mL) demonstrated recovery of 84.0% to 119.8% (mean recovery=100.7%; FIG. 8). The average percent coefficient of variation (% CV) was 6.9%. These findings indicate that this SOMAmer assay can accurately detect EGFR ECD in serum of untreated individuals.

We tested interference from 2 widely used EGFR ECD-targeting monoclonal antibody drugs (cetuximab and panitumumab) with both the SOMAmer assay and a commercially available ELISA. Pre-incubation of serum with cetuximab or panitumumab lowered the recovery of EGFR SOMAmer in a dose-dependent manner, but did not notably affect ELISA results (FIG. 9). These findings suggest that the EGFR SOMAmer detects primarily the drug-unbound fraction of EGFR in serum containing cetuximab or panitumumab.

We also performed the SOMAmer EGFR assay on samples from 3 patients with known treatment history and drug response. The results are summarized in the Table 1.

TABLE 1

Total and Unbound EGFR Levels in Patients With Metastatic Colon Cancer

| Patient | ELISA Total EGFR, ng/mL | SOMAmer Unbound EGFR, ng/mL | % Unbound EGFR | Drug | Drug Response |
|---|---|---|---|---|---|
| 1 | 285 | 15 | 5 | Panitumumab | Partial |
| 2 | 105 | 75 | 71 | Panitumumab | Partial |
| 3 | 113 | 6 | 5 | Cetuximab | Complete |

This SOMAmer-based assay can accurately measure EGFR in serum of patients not receiving anti-EGFR therapy. Whereas the EGFR ELISA measures drug-bound and unbound EGFR, the EGFR SOMAmer assay detects primarily unbound EGFR in patients receiving cetuximab or panitumumab treatment. High levels of unbound drug could be an indicator of poor interaction between drug and target.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. An aptamer comprising the nucleotide sequence:
XGANNGNNYGANNCNN (SEQ ID NO: 55);
wherein
X is a G, C or A;
Y is a G or A; and
N is, independently a 5-position modified 2'-deoxyuridine selected from the group consisting of 5-(N-benzylcarboxyamide)-2'-deoxyuracilyl, 5-(N-isobutylcarboxamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, and 5-(N-[1-(2,3-dihydroxypropyl)]carboxyamide)-2'-deoxyuridine.

2. The aptamer of claim 1, wherein said 5-position modified 2'-deoxyuridine is a 5-(N-benzylcarboxyamide)-2'-deoxyuridine (BndU).

3. The aptamer of claim 1, wherein the aptamer is capable of binding to Epidermal Growth Factor receptor (EGFR).

4. The aptamer of claim 3, wherein the binding of the aptamer to EGFR is reduced in a dose-dependent manner based on the presence of an EGFR antagonist.

5. The aptamer of claim 4, wherein the EGFR antagonist is selected from the group consisting of cetuximab and panitumumab.

6. The aptamer of claim 4, wherein the $K_d$ of the aptamer to EGFR is at least 10-fold greater based on the presence of the EGFR antagonist relative to the $K_d$ of the aptamer to free EGFR.

7. The aptamer of claim 4, wherein the $K_d$ of the aptamer to EGFR is at least $10^2$-fold greater based on the presence of the EGFR antagonist relative to the $K_d$ of the aptamer to free EGFR.

8. The aptamer of claim 1, wherein the aptamer binds to the extracellular domain of EGFR.

9. An aptamer that binds to EGFR comprising a nucleotide sequence selected from the group consisting of SEQ. ID. NOS: 1-54.

10. An aptamer that binds EGFR comprising a nucleotide sequence having at least 90% identity to anyone of the nucleotide sequences of SEQ ID NOs: 1-54.

* * * * *